(12) United States Patent
Lombardo et al.

US010876066B2

(10) Patent No.: US 10,876,066 B2
(45) Date of Patent: Dec. 29, 2020

(54) ENHANCED PERFUME COMPOSITIONS

(71) Applicant: TAKASAGO INTERNATIONAL CORPORATION, Tokyo (JP)

(72) Inventors: Louis J. Lombardo, Washingtonville, NY (US); Angelique Nadau, Westwood, NJ (US); Kimberly Kellow, Rivervale, NJ (US); Charles Steward, Midland Park, NJ (US); Carter B. Green, Stony Point, NY (US); Jeffrey R. Schmoyer, Hillsdale, NJ (US)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 513 days.

(21) Appl. No.: 15/551,996

(22) PCT Filed: Feb. 24, 2016

(86) PCT No.: PCT/US2016/019430
§ 371 (c)(1),
(2) Date: Aug. 18, 2017

(87) PCT Pub. No.: WO2016/138186
PCT Pub. Date: Sep. 1, 2016

(65) Prior Publication Data
US 2018/0030373 A1    Feb. 1, 2018

Related U.S. Application Data

(60) Provisional application No. 62/120,157, filed on Feb. 24, 2015.

(51) Int. Cl.
| | | |
|---|---|---|
| *C11B 9/00* | (2006.01) | |
| *A61K 8/35* | (2006.01) | |
| *A61K 8/34* | (2006.01) | |
| *A61K 8/37* | (2006.01) | |
| *A61Q 13/00* | (2006.01) | |
| *A61K 8/42* | (2006.01) | |
| *A61K 8/92* | (2006.01) | |
| *A61K 8/9789* | (2017.01) | |
| *A61K 31/045* | (2006.01) | |
| *A61L 9/01* | (2006.01) | |
| *C11D 3/50* | (2006.01) | |

(52) U.S. Cl.
CPC .......... *C11B 9/00* (2013.01); *A61K 8/34* (2013.01); *A61K 8/345* (2013.01); *A61K 8/347* (2013.01); *A61K 8/35* (2013.01); *A61K 8/37* (2013.01); *A61K 8/42* (2013.01); *A61K 8/922* (2013.01); *A61K 8/9789* (2017.08); *A61K 31/045* (2013.01); *A61L 9/01* (2013.01); *A61Q 13/00* (2013.01); *C11D 3/50* (2013.01); *A61K 2800/242* (2013.01); *A61K 2800/244* (2013.01); *A61K 2800/592* (2013.01)

(58) Field of Classification Search
CPC .... A61K 2800/244; A61K 8/42; A61K 8/922; A61K 8/37; A61K 8/34; A61K 8/35; A61K 8/97; A61K 2800/242; A61K 2800/75; A61K 8/345; A61K 8/347; A61K 2800/592; A61K 31/045; A61K 31/11; A61K 8/39; A61K 8/585; A61K 8/891; A61K 8/894; A23G 4/06; A23G 3/36; A23G 4/068; A23G 4/20; A23G 1/32; A23G 1/42; A23G 4/00; A23G 4/066; A23G 4/12; A23G 4/205; A61Q 13/00; A61Q 11/00; A61Q 5/02; A61Q 17/00; A61Q 5/006; A61Q 19/00; A61Q 19/10; A23L 27/204; C07C 43/196; C07C 2601/14; C07C 2101/14; C07C 69/732; C07C 69/734; A61L 9/01; C11B 9/00; C11D 3/50; A23V 2002/00; A23V 2200/15

See application file for complete search history.

(56) References Cited

U.S. PATENT DOCUMENTS

| | | |
|---|---|---|
| 4,874,536 A | 10/1989 | Strickland, Jr. et al. |
| 5,773,410 A | 6/1998 | Yamamoto |
| 6,673,844 B2 | 1/2004 | Kumamoto et al. |
| 6,790,408 B2 | 9/2004 | Whitby et al. |
| 8,071,531 B2 | 12/2011 | Aida et al. |
| 8,210,448 B2 | 7/2012 | Kvietok et al. |
| 8,377,458 B2 | 2/2013 | Komatsuki et al. |
| 8,603,963 B1 | 12/2013 | Steward et al. |
| 8,695,891 B2 | 4/2014 | Santini et al. |
| 8,741,958 B2 | 6/2014 | Lombardo et al. |
| 8,833,366 B2 | 9/2014 | Colombo et al. |
| 2002/0054893 A1 | 5/2002 | Ishida et al. |
| 2003/0215532 A1 | 11/2003 | Nakatsu et al. |
| 2004/0052735 A1* | 3/2004 | Nakatsu .................. A23G 3/36 424/49 |
| 2006/0249167 A1 | 11/2006 | Giersch et al. |
| 2009/0185951 A1 | 7/2009 | Litten-brown et al. |
| 2010/0280110 A1 | 11/2010 | Hojo et al. |
| 2010/0303740 A1 | 12/2010 | Hojo et al. |

(Continued)

FOREIGN PATENT DOCUMENTS

| | | |
|---|---|---|
| EP | 0 462 643 A1 | 12/1991 |
| EP | 0 694 514 A2 | 1/1996 |

(Continued)

OTHER PUBLICATIONS

Cain, "Contribution of the Trigeminal Nerve to Perceived Odor Magnitude," Annals New York Academy of Sciences 237:28-34 (1974).

(Continued)

*Primary Examiner* — Aaron J Kosar

(74) *Attorney, Agent, or Firm* — Baker Botts L.L.P.

(57) ABSTRACT

The presently disclosed subject matter provides fragrance compositions and fragrance combinations that can stimulate the trigeminal system. The compositions and combinations of the presently disclosed subject matter can include both one or more trigeminal-stimulating compounds and one or more additional fragrance compounds. The trigeminal-stimulating compounds can include cooling, warming, and tingling compounds.

13 Claims, 10 Drawing Sheets

(56) References Cited

U.S. PATENT DOCUMENTS

| | | |
|---|---|---|
| 2011/0117147 A1 | 5/2011 | Ishida et al. |
| 2012/0312893 A1 | 12/2012 | Santini et al. |
| 2014/0048614 A1 | 2/2014 | Santini et al. |
| 2014/0219931 A1 | 8/2014 | Komatsuki et al. |
| 2014/0328771 A1 | 11/2014 | Tanaka et al. |

FOREIGN PATENT DOCUMENTS

| | | |
|---|---|---|
| EP | 0 775 741 A1 | 5/1997 |
| EP | 1 215 257 A2 | 6/2002 |
| EP | 2 810 663 A1 | 12/2014 |
| GB | 2 178 442 A | 2/1987 |
| JP | 2001-279227 A | 10/2001 |
| JP | 2007-516316 A | 6/2007 |
| JP | 2010-254621 A | 11/2010 |
| JP | 2013-091630 A | 5/2013 |
| WO | WO 01/94520 A2 | 12/2001 |
| WO | WO 02/40792 A1 | 5/2002 |
| WO | WO 2005/042680 A1 | 5/2005 |
| WO | WO 2013/031932 A1 | 3/2013 |

OTHER PUBLICATIONS

Green et al., "Evaluating the 'Labeled Magnitude Scale' for Measuring Sensations of Taste and Smell," Chem. Senses 21:323-334 (1996).

International Search Report dated May 6, 2016 in International Application No. PCT/US16/19430.

Jacquot et al., "Influence of nasal trigeminal stimuli on olfactory sensitivity," C.R. Biologies 327:305-311 (2004).

Surfactant Science Series vol. 67 Liquid Detergents, chapter on Specialty Liquid Household Surface Cleaners p. 479, Table 4 (1997).

Supplementary European Search Report dated Jul. 9, 2018 in Application No. EP 16756317.0, 7 pages.

* cited by examiner 6A vs Control Comparison after Using Each for
14 days: Which did you NOT get tired of as quickly?

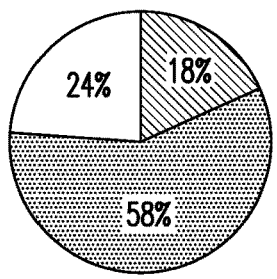

Significant @ 95% Level of Confidence

▨ Herbal Gourmand without TSC

▦ Herbal Gourmand 6A with TSC

☐ neither / both were same

FIG. 6A 6A vs Control Comparison after Using Each for
14 days: Which was more relaxing and calming?

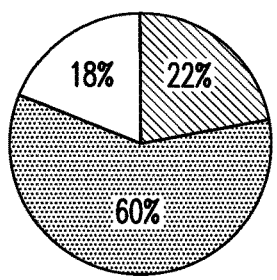

Significant @ 95% Level of Confidence

▨ Herbal Gourmand without TSC

▦ Herbal Gourmand 6A with TSC

☐ neither / both were same

FIG. 6B 6A vs Control Comparison after Using Each for
14 days: Which was more energizing and uplifting?

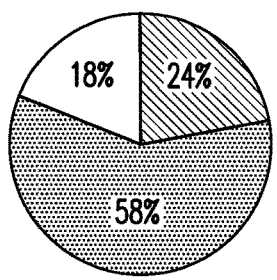

Significant @ 95% Level of Confidence

▨ Herbal Gourmand without TSC

▦ Herbal Gourmand 6A with TSC

☐ neither / both were same

FIG. 6C 6B vs Control Comparison after Using Each for
14 days: Which did you NOT get tired of as quickly?

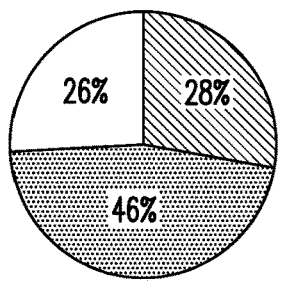

Significant @ 90% Level of Confidence

☒ Herbal Gourmand without TSC

▦ Herbal Gourmand 6A with TSC

☐ neither / both were same

FIG. 6D 6B vs Control Comparison after Using Each for
14 days: Which was more uplifting and energizing?

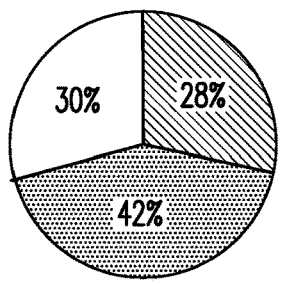

Significant @ 80% Level of Confidence

☒ Herbal Gourmand without TSC

▦ Herbal Gourmand 6A with TSC

☐ neither / both were same

FIG. 6E 6B vs Control Comparison after Using Each for
14 days: Which made your home feel more welcoming?

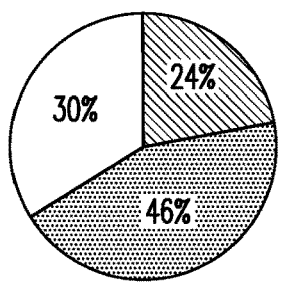

Significant @ 90% Level of Confidence

☒ Herbal Gourmand without TSC

▦ Herbal Gourmand 6A with TSC

☐ neither / both were same

FIG. 6F

ENHANCED PERFUME COMPOSITIONS

CROSS-REFERENCE TO RELATED APPLICATIONS

This application is a U.S. National Stage Patent Application under 35 U.S.C. § 371 of International Application No. PCT/US2016/019430, filed on Feb. 24, 2016, which claims priority to U.S. Provisional Patent Application Ser. No. 62/120,157, filed Feb. 24, 2015, the contents of each of which are incorporated by reference herein in their entirety.

FIELD

The presently disclosed subject matter relates to fragrance compositions and combinations of fragrance compositions. These fragrance compositions have improved performance due to the presence of compounds that can stimulate the trigeminal system.

BACKGROUND

There is continuing interest in the preparation of fragrance compositions and in the use of such compositions in consumer products. Shortcomings of existing fragrance compositions can be limited intensity, noticeability, and perceptibility. For example, certain fragrance compositions can have appealing odors but can have limited intensity and high perception thresholds, which can limit the impact of the fragrance composition at distance from its source. Other fragrance compositions can have greater intensity and lower perception thresholds but can have less appealing odors. Moreover, fragrance compositions can become less noticeable due to a user's decrease in sensitivity over prolonged exposure. Adaptation and habituation can necessitate replacement of the fragrance source.

U.S. Pat. No. 6,790,408 attempted to solve the problem of habituation through the use of a delivery device which transmitted one fragrance continuously and a second fragrance periodically. Other efforts to solve the problem through use of specially designed delivery devices are described in U.S. Pat. No. 8,210,448 (reciting the use of a device for emitting two volatile compositions in an alternating sequence) and U.S. Patent Application Publication No. 2009/0185951 (teaching the use of forced air current in a device to disseminate multiple volatile liquids located in different reservoirs). However, each of these inventions focused on the physical delivery device, or number of fragrance compositions, not the components of the compositions themselves, to prevent habituation.

Fragrance compositions typically comprise one or more fragrance compounds and/or a support material, e.g., solvent. Fragrance compositions, as well as fiber products, clothing and medicines comprising cooling sensation agents are disclosed in U.S. Pat. No. 8,377,458, to impart long-lasting cooling sensations to the user. Warming sensation agents have also been incorporated into consumer products to provide a user with a long-lasting warming effect. See, U.S. Pat. No. 6,673,844. While these prior art references result in long-lasting sensational effects, there is no reference to their ability to prevent adaptation or habituation.

An object of the present invention is to provide fragrance compositions, deliverable by various consumer products and delivery devices, with appealing odors and improved adaptability and habituation thresholds.

SUMMARY

The presently disclosed subject matter provides fragrance compositions as well as combinations of fragrance compositions. In one embodiment, an exemplary fragrance composition can include one or more trigeminal-stimulating compounds and an additional fragrance compound. In a further embodiment, the one or more trigeminal-stimulating compounds comprises two cooling compounds and a warming compound. The fragrance composition can include between about 1% and about 50% trigeminal-stimulating compound(s), or between about 5% and about 15% trigeminal-stimulating compound(s). The fragrance composition can further include one or more support materials.

In one embodiment, an exemplary fragrance combination can include a first fragrance composition that includes one or more trigeminal-stimulating compounds and a second fragrance composition that includes an additional fragrance compound.

The one or more trigeminal-stimulating compounds can include one or more of a cooling compound, a warming compound, and/or a tingling compound.

The one or more trigeminal-stimulating compounds can include a cooling compound. The one or more cooling compounds can be selected from the group consisting of menthol, menthone, camphor, pulegol, isopulegol, menthyl lactate, p-menthane-3,8-diol, mint oil, and combinations thereof.

The one or more trigeminal-stimulating compounds can include a warming compound. The warming compound can include one or more warming compounds selected from the group consisting of vanillyl ethyl ether, vanillyl propyl ether, vanillyl butyl ether, vanillin, vanillyl alcohol, ethyl vanillin, ethyl vanillyl alcohol, and combinations thereof.

The trigeminal-stimulating compound can include a tingling compound. The tingling compound can include jambu oleoresin, spilanthol, and combinations thereof.

The foregoing has outlined rather broadly the features and technical advantages of the present application in order that the detailed description that follows may be better understood. Additional features and advantages of the application will be described hereinafter which form the subject of the claims of the application. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

BRIEF DESCRIPTION OF THE DRAWINGS

FIG. 1a depicts the hedonics of formulation 6A with and without TSC measured on a scale of 1-9 over 72 minutes. FIG. 1b depicts the hedonics of formulation 6B with and without TSC, measured on a scale of 1-9 over 72 minutes.

FIG. 5a depicts the overall liking opinion of formulation 6A with and without TSC. FIG. 5b depicts the overall liking opinion of formulation 6B with and without TSC. Mean scores with standard error of means are shown.

FIGS. 6a-6f depict comparison preferences of the products tested in Example 10. Specifically, FIG. 6a illustrates which product formulated with 6A the consumer did not tire of as quickly. FIG. 6b illustrates which product formulated with 6A was more relaxing and calming. FIG. 6c illustrates which product formulated with 6A made the consumers' home feel more welcoming. FIG. 6d illustrates which product formulated with 6B the consumer did not tire of as quickly.

FIG. 6e illustrates which product formulated with 6B was more uplifting and energizing. FIG. 6f illustrates which product formulated with 6B made the consumers' home feel more welcoming.

FIG. 7 depicts the overall liking opinion of a clean/laundry type fragrance with and without TSC. Mean scores with standard error of means are shown.

FIG. 8 depicts the overall liking opinion of a fruity/floral type fragrance with and without TSC. Mean scores with standard error of means are shown.

FIG. 9a illustrates which product the consumer did not tire of as quickly. FIG. 9b illustrates which product the consumer found more light and airy.

DETAILED DESCRIPTION

Figure 1A:
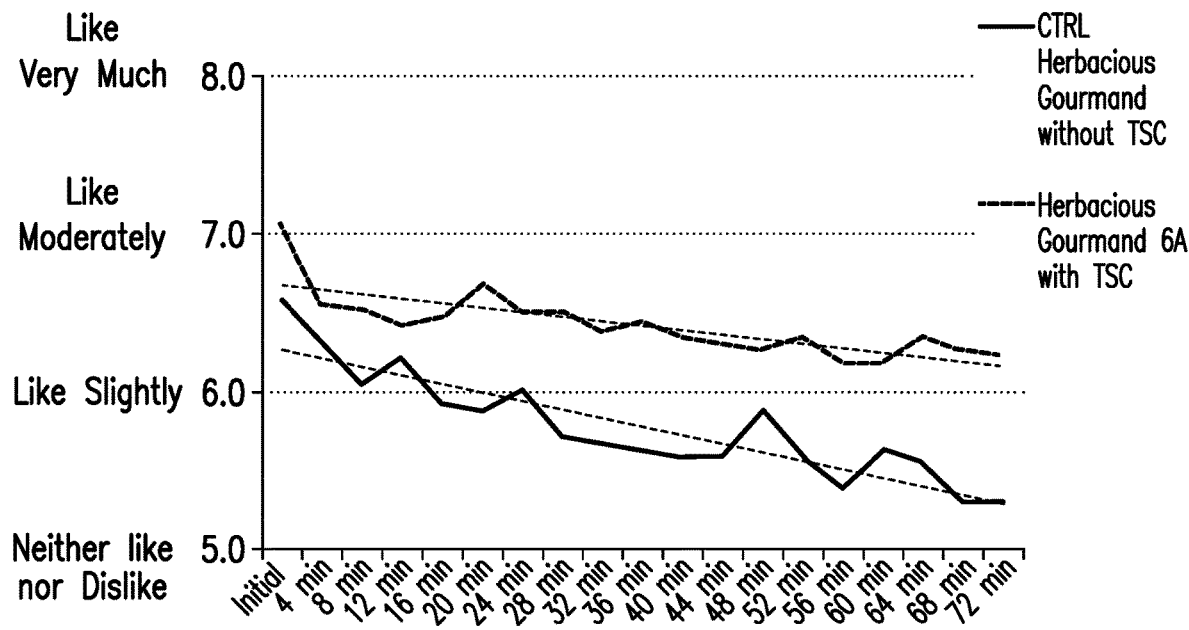
FIGS. 1a-1b depict the results of Example 6.

As noted above, there remains a need for fragrance compositions with appealing odors and improved intensity, noticeability, and perception thresholds. The present disclosure provides fragrance compositions and combinations of fragrance compositions that have such properties. It has surprisingly been found that inclusion of one or more trigeminal-stimulating compounds into a fragrance composition can improve the hedonic experience, intensity, and noticeability of the odor, alone or in combination with a second fragrance composition. Inclusion of one or more trigeminal-stimulating compounds can also lower the perception threshold of a user, allowing the odor to be perceived at a greater distance from its source. In certain embodiments, the trigeminal-stimulating compounds of the presently disclosed subject matter can improve intensity, noticeability and perception thresholds of a fragrance composition over a user's period of exposure. The trigeminal-stimulating compounds of the present disclosure can include, but are not limited to, cooling materials, warming materials, and tingling materials.

For clarity, and not by way of limitation, the detailed description is divided into the following subsections: I. Definitions; II. Trigeminal-Stimulating Compounds; and III. Fragrance Compositions, Combinations, and Products.

I. Definitions

As used herein, the words "a" or "an," when used in conjunction with the term "comprising" in the claims and/or the specification, may mean "one," but they are also consistent with the meaning of "one or more," "at least one," and/or "one or more than one." Furthermore, the terms "having," "including," "containing" and "comprising" are interchangeable, and one of skill in the art will recognize that these terms are open ended terms.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

As used herein, "fragrance" can also be used interchangeably with aroma, scent or odor.

As used herein, the term "intensity" can describe the extent or degree to which an olfactory stimulus can be perceived as measured by a variety of scales known to those skilled in the art, including, the Labeled Magnitude Scale (LMS). The LMS is considered to be a more true representation of the magnitude of a consumer's perception. See, B. Green et al., *Chem. Senses* 21(3): 323-334 (1996).

As used herein, the term "strength" can be used interchangeably with "intensity" in the consumer and expert sensory panelist vernacular.

As used herein, the term "olfactory preference" can describe a user or tester's subjective experience of the quality or appeal of a fragrance, e.g., the desire to select one fragrance over another.

As used herein, the term "liking" or "hedonics" can describe a user or tester's subjective overall experience of a fragrance. "Liking" can encompass both the intensity and olfactory preference of the fragrance.

As used herein, the phrase "tire of" can describe a consumer no longer having the same preference for a fragrance as when the consumer began using it. The phrase "tire of" can be synonymous with "weary of."

As used herein, the term "adaptation" can describe a user or tester's decreased sensitivity to an odor from the continuous smelling of a fragrance composition or a fragrance combination responsible for the odor. Without being bound to any particular theory, adaptation can be thought to occur from short-term processing via sensory neurons in the olfactory system to attenuate an odor signal.

As used herein, the term "habituation" can describe a user or tester's long-term loss of awareness of a background odor. Habituation can be considered a form of learning that can arise from prolonged exposure to an odor. Habituation can be related to adaptation. Like adaptation, habituation can result in lower sensitivity to an odor, as a lower level of attention is directed to the odor.

As used herein, the terms "trigeminal-stimulating compounds" and "compounds that stimulate the trigeminal system" refer to compounds that can stimulate or activate the intranasal trigeminal system and, specifically, the trigeminal nerve. See, W. S. Cain, *Annals New York Academy of Sciences* 237:28-34 (1974). The trigeminal nerve is part of the nervous system. The trigeminal system also includes nasal cavity surface receptors, pathways and sensory fibers which conduct from the trigeminal nerve to the brain. Trigeminal nerves, sensory nerves, and epithelial cells mediate chemesthetic taste and fragrance or taste and aroma sensations which can be caused by chemical activation of ion channels. Trigeminal-stimulating compounds can induce a variety of different sensations by activation of these ion channels. By way of non-limiting example, sensations induced by trigeminal-stimulating compounds can include irritation, tickling, burning, stinging, tingling, warming, cooling, and/or astringency. Transient receptor potential (TRP) channels impacted by trigeminal-stimulating compounds include TRPV (inducing a warming sensation), TRPA (inducing a tingling or irritating sensation) and TRPM (inducing a cooling sensation). Trigeminal-stimulating compounds can also be known as chemesthetic compounds or chemesthetic agents.

Certain trigeminal-stimulating compounds, when used at levels below a certain threshold ("sub-threshold levels"), can stimulate the user's trigeminal system in such a way that the user perceives a sensation not specifically identifiable as irritation, tickling, burning, stinging, tingling, warming, cooling, astringency, etc. Without being bound to any particular theory, it can be that when used at sub-threshold levels in conjunction with other fragrance materials, certain trigeminal-stimulating compounds can influence the fragrance perceived by a user despite not being individually identifiable as irritating, tickling, burning, stinging, tingling, warming, cooling, or astringent agents.

II. Trigeminal-Stimulating Compounds

Trigeminal-stimulating compounds can impart various sensations to the mucous membranes, including the oral cavity, nasal cavity, throat, and/or skin. See, L. Jacquot et al., *C. R. Biologies* 327:305-311 (2004). In certain embodiments, the trigeminal-stimulating compound can be a cooling compound, a warming compound, and/or tingling compound. Two or more trigeminal-stimulating compounds can be combined.

Trigeminal-stimulating compounds can be naturally or synthetically derived. Both naturally derived and synthetically derived trigeminal-stimulating compounds can be used in conjunction with the presently disclosed subject matter. In certain embodiments, the trigeminal-stimulating compounds can be entirely naturally derived, entirely synthetically derived, or a mixture of naturally derived and synthetically derived compounds. In certain embodiments, the trigeminal-stimulating compounds can include racemates and isomers. In certain embodiments, the trigeminal-stimulating compounds can have an optical isomer and chemical purity of greater than 90%, preferably greater than 95%, more preferably greater than 97.5%, and even more preferably greater than 99%. Purity can be determined by gas chromatography using the method described in U.S. Pat. No. 5,773,410 by summing the area percent of impurity peaks and subtracting these from the total measured area which is taken to be 100%.

By way of non-limiting example, cooling trigeminal-stimulating compounds can include, but are not limited to, menthol, menthone, methyl acetate, camphor, pulegol, isopulegol (COOLACT® P) (CAS 89-79-2), cineole, 2-isopropyl-N-2,3-trimethylbutyramide, N-ethyl-2-isopropyl-5-methylcyclohexane carboxamide, ethyl 3-(p-menthane-3-carboxamido)acetate, N-(4-methoxyphenyl)-p-menthanecarboxamide, N-ethyl-2,2-diisopropylbutanamide, N-cyclopropyl-5-methyl-2-isopropylcyclohexanecarboxamide, N-(1,1-dimethyl-2-hydroxyethyl)-2,2-diethylbutanamide, N-(4-cyanomethylphenyl)-p-menthanecarboxamide, N-(2-(Pyridin-2-yl)ethyl)-3-p-menthanecarboxamide, N-(2-hydroxyethyl)-2-isopropyl-2,3-dimethylbutanamide, cyclopropanecarboxylic acid (2-isopropyl-5-methylcyclohexyl)-amide, N-[4-(2-Amino-2-oxoethyl)phenyl]-p-menthanecarboxamide, menthyl pyrrolidone carboxylate, cubebol, icilin, 2-isopropyl-5-methylcyclohexyl 4-(dimethylamino)-4-oxobutanoate, N-benzo[1,3] dioxol-5-yl-3-p-menthanecarboxamide, N-benzooxazol-4-yl-3-p-menthane-carboxamide, N-4-([1,2,4]triazol-1-yl)-phenyl-3-p-menthanecarboxamide, p-menthane carboxamides, N-4-(pyrazol-1-yl)-phenyl-3-p-menthanecarboxamide, N-(1-isopropyl-1,2-dimethylpropyl)-1,3-benzodioxole-5-carboxamide, N-(1-methyl-1-isopropylbutyl)benzamide, fenchyl-N,N-dimethylsuccinamide, fenchyl monosuccinate, ethyl fenchyl malonate, bornyl monosuccinate, isobornyl monosuccinate, menthyl 3-oxobutyrate, menthyl 3-oxopentanoate, 3-1-menthoxypropane-1,2-diol, 3-1-menthoxy-2-methylpropane-1,2-diol, p-menthane-3,8-diol (COOLACT® 38D), 2-1-menthoxyethan-1-ol, 3-1-menthoxypropan-1-ol, 4-1-menthoxybutan-1-ol, menthyl 3-hydroxybutyrate, 6-isopropyl-9-methyl-1,4-dioxaspiro-(4,5)-decane-2-methanol, 2-[(2-p-menthoxy)ethoxy]ethanol, menthyl succinate, menthyl glutarate, dimenthyl succinate, dimenthyl glutarate, menthyl lactate, menthone glycerin ketal, mint oil, peppermint oil, spearmint oil, eucalyptus oil, 1-(2-hydroxy-4-methylcyclohexyl)ethanone (COOLACT° HK), and all stereoisomers and mixtures thereof. In certain embodiments, cooling trigeminal-stimulating compounds can include menthol, menthone, camphor, pulegol, isopulegol, menthyl lactate, p-menthane-3,8-diol, mint oil, or a mixture thereof. In certain embodiments, cooling trigeminal-stimulating compounds can include 1-(2-hydroxy-4-methylcyclohexyl)ethanone (COOLACT® HK). Preparation and properties of 1-(2-hydroxy-4-methylcyclohexyl) ethanone are disclosed in U.S. Pat. No. 8,071,531, the contents of which are hereby incorporated by reference in their entirety.

By way of non-limiting example, warming trigeminal-stimulating compounds can include, but are not limited to, vanillyl ethyl ether (HOTACT® VEE), vanillyl propyl ether, vanillin propylene glycol acetal, ethyl vanillin propylene glycol acetal, capsaicin, gingerol, vanillyl butyl ether (HOTACT® VBE), 4-(1-menthoxy-methyl)-2-phenyl-1,3-dioxolane, 4-(1-menthoxy-methyl)-2-(3',4'-dihydroxy-phenyl)-1,3-dioxolane, 4-(1-menthoxy-methyl)-2-(2'-hydroxy-3'-methoxy-phenyl)-1,3-dioxolane, 4-(1-menthoxy-methyl)-2-(4'-methoxyphenyl)-1,3-dioxolane, 4-(1-menthoxy-methyl)-2-(3'4'-methylenedioxy-phenyl)-1,3-dioxolane, hot pepper oil, capsicum oleoresin, ginger oleoresin, nonyl acid vanillylamide, 4-(1-menthoxy-methyl)-2-(3'-methoxy-4'-hydroxyphenyl)-1,3-dioxolane, vanillin-1,2-hexylene glycol acetal, vanillin-1,2-butylene glycol acetal, vanillin-1-butoxyglycerol acetal, ethyl vanillin, ethyl vanillyl alcohol (3-ethoxy-4-hydroxybenzyl alcohol); homovanillyl acids, esters, and amines; ethyl vanillyl ethers, vanillin, vanillyl alcohol, and all stereoisomers and mixtures thereof. In certain embodiments, warming trigeminal-stimulating compounds can include vanillyl ethyl ether, vanillyl propyl ether, vanillyl butyl ether, vanillin, vanillyl alcohol, ethyl vanillin, ethyl vanillyl alcohol, or a mixture thereof.

By way of non-limiting example, tingling trigeminal-stimulating compounds can include, but are not limited to, spilanthol, sanshool, hydroxy γ-sanshool, hydroxy-sanshool, hydroxy γ-sanshool, sanshool-I, sanshool II, sanshoamide, Japanese pepper extract, black pepper extract, chavicine, piperine, echinacea extract, northern prickly ash extract, Nepalese spice timur extract, red pepper oleoresin, 4-(1-menthoxymethyl)-2-phenyl-1, 3-dioxolane, N-isobutyldeca-(2,4)-dienamide, N-cyclopropyl-(2E,6Z)-nonadienamide, N-ethyl-(2E,6Z)-nonadienamide, jambu oleoresin, vanillyl ethyl ether, vanillyl n-propyl ether, vanillyl isopropyl ether, vanillyl butyl ether, elemol, elimicin, lime oxide, elemi oil, ocimene quintoxide, 2-isopropenyl-5-methyl-5-vinyltetrahydrofuran, isopulegol, and all stereoisomers and mixtures thereof. U.S. Pat. No. 8,741,958 discloses synthesis of synthetic spilanthol, the contents of which is hereby incorporated by reference in its entirety. In certain embodiments, the tingling trigeminal-stimulating compound can be spilanthol, jambu oleoresin, and combinations thereof.

By way of non-limiting example, irritating trigeminal-stimulating compounds can include, but are not limited to, black pepper extract, allyl-isothiocyanate, 4-hydroxybenzyl isothiocyanate, capsicum oleoresin, mustard oil, cinnamaldehyde, capsaicin, wasabi extract, red pepper oleoresin, oleocanthal, and combinations thereof.

Trigeminal-stimulating compounds suitable for use in the compositions of the presently disclosed subject matter can have characteristic physical and/or chemical properties. By way of non-limiting example, trigeminal-stimulating compounds can have characteristic molecular weights, boiling points, or vapor pressures. In certain embodiments, the trigeminal-stimulating compounds can have molecular weights of greater than 100 daltons, greater than 120 daltons, or weights of less than or no more than about 250 daltons, about 300 daltons, or about 350 daltons. In certain embodiments, the trigeminal-stimulating compounds can have boiling points of from about 80° C. to about 400° C. or from about 100° C. to about 350° C. In certain embodiments, the trigeminal-stimulating compounds can have boiling points of less than or no more than about 250° C., about 300° C., or about 350° C., or about 400° C., or about 450° C. at atmospheric pressure. In certain embodiments, the trigeminal-stimulating compounds can have vapor pressures of less than or no more than about $1 \times 10^{-5}$ mm Hg, about $1 \times 10^{-4}$ mm Hg, or about $1 \times 10^{-3}$ mm Hg. Such physical and/or chemical properties can be computed by any available software, e.g., Advanced Laboratory Development Software (ACD/Labs; Toronto, Canada).

Without being bound to any particular theory, it can be that suitable trigeminal-stimulating compounds can have characteristic volatility. The compounds' volatility can be related to their physical properties, including molecular weight, boiling point, and vapor pressure. Compounds with suitable volatility can vaporize (become a gas) and be detected by a user's olfactory system, including the user's trigeminal system, at levels that improve the overall intensity and appeal of a fragrance.

Trigeminal-stimulating compositions can contain one, two, three, four or more trigeminal-stimulating compounds. In certain embodiments, a trigeminal-stimulating compositions comprises two trigeminal-stimulating compounds. In certain embodiments, a trigeminal-stimulating compositions comprises three trigeminal-stimulating compounds. In embodiments comprising two trigeminal-stimulating compounds, the trigeminal-stimulating compounds are present in a ratio. The two trigeminal-stimulating compounds can be present in a ratio of from about(0.01-60):(60-0.01), or from about (0.2-40):(40-0.2), or from about (5-1):(1-5), or from about (3-1):(1-3). In certain embodiments two trigeminal-stimulating compounds can be present in a ratio of about 59:1, about 39:1, about 35:1, about 32:1, about 3:1, about 1:1, about 0.02:1, or about 0.015:1.

In embodiments comprising three trigeminal-stimulating compounds, the three trigeminal-stimulating compounds can be present in a ratio. The three trigeminal-stimulating compounds can be present in a ratio of from about (0.01-15):(0.5-10):(0.01-15), or from about (0.01-13):(1-8):(0.01-13), or from about (0.01-2):(1-2):(0.01-2). In certain embodiments three trigeminal-stimulating compounds can be present in a ratio of about 0.01:1:1, about 1:0.07:1.8, or about 1:6.5:12.5.

III. Fragrance Compositions, Combinations, and Products

The presently disclosed subject matter provides fragrance compositions that can include one or more trigeminal-stimulating compositions, one or more fragrance compounds, and/or one or more supports.

Fragrance compositions can contain one, two, three, four or more trigeminal-stimulating compounds. Fragrance compositions can contain one, two, three, four or more trigeminal-stimulating compositions. In certain embodiments, a fragrance composition comprises two trigeminal-stimulating compounds. In certain embodiments, a fragrance composition comprises three trigeminal-stimulating compounds.

As embodied in the non-limiting Examples, trigeminal-stimulating compounds can be incorporated into fragrance compositions in various amounts. By way of non-limiting example, one or more trigeminal-stimulating compounds can be incorporated into a fragrance composition at an amount of from about 0.1% to about 60%, about 0.1% to about 10%, about 0.1% to about 5%, or about 0.1% to about 1% by weight of the total fragrance composition. In certain embodiments, one or more trigeminal-stimulating compounds can be incorporated into a fragrance composition at an amount of from about 1% to about 60%, about 5% to about 60%, about 10% to about 60%, about 20% to about 60%, or about 30% to about 60% by weight of the total fragrance composition. In certain embodiments, one or more trigeminal-stimulating compounds can be incorporated into a fragrance composition at an amount of from about 1% to about 50%, about 1% to about 40%, about 1% to about 30%, about 1% to about 20%, about 1% to about 10%, or about 1% to about 5% by weight of the total fragrance composition. In certain embodiments, one or more trigeminal-stimulating compounds can be incorporated into a fragrance composition at an amount of from about 5% to about 50%, about 5% to about 40%, or about 5% to about 30% by weight of the total fragrance composition. In certain embodiments, one or more trigeminal-stimulating compounds can be incorporated into a fragrance composition at an amount of from about 10% to about 50%, about 10% to about 40%, or about 10% to about 30% by weight of the total fragrance composition. In certain embodiments, one or more trigeminal-stimulating compounds can be incorporated into a fragrance composition at an amount of from about 20% to about 50%, about 20% to about 40%, or about 20% to about 30% by weight of the total fragrance composition. In certain embodiments, one or more trigeminal-stimulating compounds can be incorporated into a fragrance composition at an amount of from about 30% to about 50% or about 30% to about 40% by weight of the total fragrance composition. In certain embodiments, one or more trigeminal-stimulating compounds can be incorporated into a fragrance composition at an amount of about 30%, about 5% to about 15%, or about 5% to about 10% by weight of the total fragrance composition. In certain embodiments, one or more trigeminal-stimulating compounds can be incorporated into a fragrance composition at an amount of about 6.5% or about 7% or about 8.4% or about 10.1% by weight of the total fragrance composition. In certain embodiments, a fragrance composition can contain one, two, three, four or more fragrance compounds.

In certain embodiments, a fragrance composition can include three trigeminal-stimulating compounds, one or more fragrance compounds, and one support material. In certain embodiments, the support is a solvent.

Fragrance compositions of the presently disclosed subject matter can include one or more additional fragrance compounds in combination with one or more trigeminal-stimulating compounds. In certain embodiments, the fragrance composition can be a uniform composition, e.g., a homogenous solution, that includes both a trigeminal-stimulating compound and an additional fragrance compound. By way of non-limiting example, the ratio of trigeminal stimulating compound(s) to additional fragrance compound(s) within a composition can be between about 1:1000 and about 1000:1, e.g., about 1:1000, about 1:100, about 1:50, about 1:30, about 1:20, about 1:10, about 1:5, about 1:3, about 1:2, about 1:1, about 2:1, about 3:1, about 5:1, about 10:1, about 20:1, about 30:1, about 50:1, about 100:1, or about 1000:1, by weight.

Additional fragrance compounds suitable for use in conjunction with one or more trigeminal-stimulating compounds(s), both within a single fragrance composition as well as in distinct fragrance compositions, can include, but are not limited to, various esters, terpenes, aldehydes, ketones, ethers, nitriles, essential oils, other aromatics, distillates, extracts, fractions and mixtures thereof. In certain embodiments, the additional fragrance compound(s) can have a higher vapor pressure (i.e., a higher volatility) than the trigeminal-stimulating compound(s).

Non-limiting examples of fragrance compounds suitable for use include $C_8$-$C_{18}$ hydrocarbons (such as delta-3-carene, alpha-pinene, beta-pinene, alpha-terpinene, gamma-terpinene, p-cymene, bisabolene, camphene, caryophyllene, cedrene, farnesene, limonene, longifolene, myrcene, ocimene, valencene, (E,Z)-1,3,5-undecatriene); $C_2$-$C_{18}$ aliphatic alcohols (such as hexanol, octanol, 3-octanol, 2,6-dimethylheptanol, 2-methylheptanol, 2-methyloctanol, (E)-3-hexenol, (E) and (Z)-3-hexenol, 1-octen-3-ol, mixtures of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, 4-methyl-3-decen-5-ol); $C_2$-$C_{18}$ aliphatic aldehydes and their acetals, (such as hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal diethyl acetal, 1,1-dimethoxy-2,2,5-trimethyl-4-hexene, citronellyl oxyacetaldehyde); $C_3$-$C_{18}$ aliphatic ketones and oximes thereof (such as 2-heptanone, 2-octanone, 3-octanone, 2-nonanone, 5-methyl-3-heptanone, 5-methyl-3-heptanone oxime, 2,4,4,7-tetramethyl-6-octen-3-one); $C_2$-$C_{18}$ aliphatic sulphur-containing compounds (such as 3-methylthiohexanol, 3-methylthiohexyl acetate, 3-mercaptohexanol, 3-mercaptohexyl acetate, 3-mercaptohexyl butyrate, 3-acetylthiohexyl acetate, 1-menthene-8-thiol); $C_2$-$C_{18}$ aliphatic nitrile-containing compounds (such as 2-nonenenitrile, 2-tridecenenitrile, 2,12-tridecenene-nitrile, 3,7-dimethyl-2,6-octadienenitrile, 3,7-dimethyl-6-octenenitrile).

Non-limiting examples of fragrance compounds suitable for use further include $C_2$-$C_{18}$ aliphatic carboxylic acids and esters thereof (such as (E)- and (Z)-3-hexenyl formate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexyl butyrate, (E)- and (Z)-3-hexenyl isobutyrate, hexyl crotonate, ethyl isovalerate, ethyl 2-methylpentanoate, ethyl hexanoate, allyl hexanoate, ethyl heptanoate, allyl heptanoate, ethyl octanoate, ethyl (E,Z)-2,4-decadienoate, methyl 2-octynoate, methyl 2-nonynoate, allyl-2-isoamyloxyacetate, methyl-3,7-dimethyl-2,6-octadienoate); $C_4$-$C_{18}$ acyclic terpene alcohols (such as citronellol, geraniol, nerol, linalool, lavandulol, nerolidol, farnesol, tetrahydrolinalool, tetrahydrogeraniol, 2,6-dimethyl-7-octen-2-ol, 2,6-dimethyloctan-2-ol, 2-methyl-6-methylene-7-octen-2-ol, 2,6-dimethyl-5,7-octadien-2-ol, 2,6-dimethyl-3,5-octadien-2-ol, 3,7-dimethyl-4,6-octadien-3-ol, 3,7-dimethyl-1,5,7-octatrien-3-ol, 2,6-dimethyl-2,5,7-octatrien-1-ol); $C_4$-$C_{18}$ acyclic terpene aldehydes and ketones (such as geranial, neral, citronellal, 7-hydroxy-3,7-dimethyloctanal, 7-methoxy-3,7-dimethyloctanal, 2,6,10-trimethyl-9-undecenal, geranylacetone, and the dimethyl and diethyl acetals of geranial, neral, 7-hydroxy-3,7-dimethyloctanal); $C_4$-$C_{18}$ cyclic terpene alcohols (such as alpha-terpineol, terpineol-4, menthan-8-ol, menthan-1-ol, menthan-7-ol, borneol, isoborneol, linalool oxide, nopol, cedrol, ambrinol, vetiverol, guaiol); $C_4$-$C_{18}$ cyclic terpene aldehydes and ketones (such as fenchone, alpha-ionone, beta-ionone, alpha-n-methylionone, beta-n-methylionone, alpha-isomethylionone, beta-isomethylionone, alpha-irone, alpha-damascone, beta-damascone, beta-damascenone, delta-damascone, gamma-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H)-one, nootkatone, dihydronootkatone, alpha-sinensal, beta-sinensal, methyl cedryl ketone).

Non-limiting examples of fragrance compounds suitable for use further include $C_4$-$C_{18}$ cyclic alcohols (such as 4-tert-butylcyclohexanol, 3,3,5-trimethylcyclohexanol, 3-isocamphylcyclohexanol, 2,6,9-trimethyl-Z2,Z5,E9-cyclododecatrien-1-ol, 2-isobutyl-4-methyltetrahydro-2H-pyran-4-ol); $C_4$-$C_{18}$ cycloaliphatic alcohols (such as alpha-3,3-trimethylcyclohexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, 1-(2,2,6-trimethylcyclohexyl)hexan-3-ol); $C_4$-$C_{18}$ cyclic and cycloaliphatic ethers (such as cedryl methyl ether, cyclododecyl methyl ether, (ethoxymethoxy)cyclododecane, alpha-cedrene epoxide, 3a,6,6,9a-tetramethyl-dodecahydronaphtho[2,1-b]furan, 3a-ethyl-6,6,9a-trimethyldodecahydronaphtho[2,1-b]furan, 1,5,9-trimethyl-13-oxabicyclo[10.1.0]trideca-4,8-diene, rose oxide, 2-(2,4-dimethyl-3-cyclohexen-1-yl)-5-methyl-5-(1-methylpropyl)-1,3-dioxane); $C_4$-$C_{18}$ cyclic ketones (such as 4-tert-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert-pentylcyclohexanone, 5-cyclohexadecen-l-one, 6,7-dihydro-1,1,2,3,3-pentamethyl-4 (5H)-indanone, 9-cycloheptadecen-1-one, cyclopentadecanone, cyclohexadecanone); $C_4$-$C_{18}$ cycloaliphatic aldehydes (such as 2,4-dimethyl-3-cyclohexenecarbaldehyde, 2-methyl-4-(2,2,6-trimethyl-cyclohexen-1-yl)-2-butenal, 4-(4-hydroxy-4-methylpentyl)-3-cyclohexenecarbaldehyde, 4-(4-methyl-3-penten-1-yl)-3-cyclohexenecarbaldehyde); $C_4$-$C_{18}$ cycloaliphatic ketones (such as 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphthalenyl methyl ketone, methyl-2,6,10-trimethyl-2,5,9-cyclododecatrienyl ketone, tert-butyl(2,4-dimethyl-3-cyclohexen-1-yl)ketone); esters of cyclic alcohols in $C_4$-$C_{18}$ (such as 2-tert-butylcyclohexyl acetate, 4-tert-butyl-cyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl isobutyrate, 4,7-methanooctahydro-5 or 6-indenyl acetate); esters of cycloaliphatic carboxylic acids in $C_4$-$C_{18}$ (such as allyl 3-cyclohexylpropionate, allyl cyclohexyloxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, ethyl 2-methyl-1,3-dioxolane-2-acetate); $C_4$-$C_{18}$ aromatic hydrocarbons (such as styrene and diphenylmethane);

$C_4$-$C_{18}$ araliphatic alcohols (such as benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, 1-(4-isopropylphenyl)ethanol); esters of araliphatic alcohols in $C_4$-$C_{18}$ and aliphatic carboxylic acids in $C_4$-$C_{18}$ (such as benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, alpha-trichloromethylbenzyl acetate, alpha,alpha-dimethylphenylethyl acetate, alpha,alpha-dimethylphenylethyl butyrate, cinnamyl acetate, 2-phenoxyethyl isobutyrate, 4-methoxybenzyl acetate); $C_2$-$C_{18}$ araliphatic ethers (such as 2-phenylethyl methyl ether, 2-phenylethyl isoamyl ether, 2-phenylethyl 1-ethoxyethyl ether, phenylacetaldehyde dimethyl acetal, phenylacetaldehyde diethyl acetal, hydratropaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, 4,4a,5,9b-tetrahydro-2,4-dimethylindeno[1,2-d]-m-dioxin); $C_4$-$C_{18}$ aromatic and araliphatic aldehydes (such as benzaldehyde, phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert.-butylphenyl)propanal, 3-(4-tert-butylphenyl)propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylenedioxybenzaldehyde, 3,4-dimethoxybenzaldehyde, 2-methyl-3-(4-methoxyphenyl)propanal, 2-methyl-3-(4-methylenedioxyphenyl)propanal.

Non-limiting examples of fragrance compounds suitable for use further include $C_4$-$C_{18}$ aromatic and araliphatic ketones (such as acetophenone, 4-methylacetophenone, 4-methoxyacetophenone, 4-tert-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert-butyl-1,1-dimethyl-4-indanyl methyl ketone, 1-[2,3-dihydro-1,1,2,6-tetramethyl-3-(1-methylethyl)-1H-5-indenyl]ethanone, 5',6',7',8'-tetrahydro-3',5',5',6',8',8'-hexamethyl-2-acetonaphthone); $C_4$-$C_{18}$ aromatic and araliphatic carboxylic acids and esters thereof (such as phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, ethyl 3-methyl-3-phenylglycidate); nitrogen-containing aromatic compounds in $C_4$-$C_{18}$ (such as 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenenitrile, 5-phenyl-3-methylpentanenitrile, methyl anthranilate, methyl N-methylanthranilate, Schiff bases of methyl anthranilate with 7-hydroxy-3,7-dimethyloctanal, 2-methyl-3-(4-tert-butylphenyl)propanal, 2,4-dimethyl-3-cyclohexene-carbaldehyde, 6-isopropylquinoline, 6-isobutylquinoline, 6-sec-butylquinoline, indole, skatole, 2-methoxy-3-isopropylpyrazine, 2-isobutyl-3-methoxypyrazine); phenols, phenyl ethers and phenyl esters (such as estragole, anethole, eugenol, eugenyl methyl ether, isoeugenol, isoeugenyl methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, p-cresyl phenylacetate); heterocyclic compounds in $C_4$-$C_{12}$ (such as 2,5-dimethyl-4-hydroxy-2H-furan-3-one, 2-ethyl-4-hydroxy-5-methyl-2H-furan-3-one, 3-hydroxy-2-methyl-4H-pyran-4-one, 2-ethyl-3-hydroxy-4H-pyran-4-one); lactones in $C_4$-$C_{12}$ (such as 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis and trans-11-pentadecen-1,15-olide, cis- and trans-12-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene 1,12-dodecanedioate, ethylene 1,13-tridecanedioate, coumarin, 2,3-dihydrocoumarin, octahydrocoumarin).

In certain embodiments, the presently disclosed fragrance compositions can include one or more support materials. By way of non-limiting example, support materials can include but are not limited to solvents (including oils), waxes, sugars, UV stabilizers and resins. Suitable solvents can include those known in the art for use in fragrance compositions. By way of non-limiting example, suitable solvents can include propylene glycol, dipropylene glycol, triethyl citrate, benzyl alcohol, benzyl benzoate, isopropyl myristate, dipropylene glycol methyl ether acetate (DPMA), ethanol, vegetable oils, essential oils, orange terpenes, those sold under the trade name Isopar , dialkyl adipates, dialkyl succinates, dialkyl glutarates, (such as the dimethyl esters sold under the trade name Flexisolv), citrate esters (such as acetyl triethyl citrate and acetyl tributyl citrate), diethyl phthalate, diethylene glycol monoethyl ether, 3-methoxy-3-methyl-1-butanol, isopropylidene glycerol sold under the trade name AugeoTM and combinations thereof. Suitable support materials are also disclosed by U.S. Pat. No. 8,603,963, the contents of which is hereby incorporated by reference in its entirety. By way of non-limiting example, suitable waxes can include paraffin, beeswax, soy wax, and stearin. By way of non-limiting example, suitable sugars can include sucrose, mannitol, maltose, isomaltose, and trehalose. By way of non-limiting example, suitable resins can include polyacrylates, polyesters, polyvinyl chlorides (PVCs), and polyolefins. Non-limiting examples of UV stabilizers include those sold under the trade name Uvinol®.

Fragrance compositions of the presently disclosed subject matter that include one or more trigeminal-stimulating compounds can be used in combination with one or more distinct additional compositions that include other fragrance compounds. In certain embodiments, a first fragrance composition containing one or more trigeminal-stimulating compounds and a second fragrance composition containing one or more additional fragrance compounds can be prepared, and the two compositions can be used in combination. In certain embodiments, a combination that includes a first fragrance composition that includes one or more trigeminal-stimulating compounds and a second fragrance composition that includes one or more additional fragrance compounds can be presented to a user. In certain embodiments, the first fragrance composition can be presented to a user first, and the second fragrance composition can be presented subsequently, or the second fragrance composition can be presented to a user first, and the first fragrance composition can be presented subsequently.

In certain embodiments wherein a fragrance composition that includes at least one trigeminal-stimulating compound and at least one additional fragrance compound is used, the composition can produce an air-space experienced by a user. Air-space is considered in relation to a product containing the fragrance composition which includes at least one trigeminal-stimulating compound and/or at least one fragrance composition. The air-space can include both trigeminal-stimulating compound(s) as well as additional fragrance compound(s). Similarly, in certain embodiments wherein a fragrance combination that includes a first fragrance composition containing one or more trigeminal-stimulating compounds and a second fragrance composition containing one or more additional fragrance compounds is used, the combination can produce an air-space experienced by a user. The air-space can include both trigeminal-stimulating compound(s) as well as additional fragrance compound(s).

The ratio of trigeminal-stimulating compound(s) to additional fragrance compound(s) in the air-space experienced by a user can vary. The concentration of trigeminal-stimulating compound(s) and fragrance compound(s) in the air-space can vary in based on many factors such as room size (small (e.g., a bath or living room) or large areas (e.g., large commercial and recreational spaces)), room temperature, air circulation, and different evaporation rates of different compounds. Therefore, the amounts of each component present can be calculated both by weight percent and by mole percent for components in the vapor phase as well as in solvent. By way of non-limiting example, the ratio of trigeminal-stimulating compound(s) to additional fragrance compound(s) in the air can be between about 1:100 and about 1:1, between about 1:100 and about 1:2, between about 1:100 and about 1:5, between about 1:100 and about 1:10, between about 1:100 and about 1:20, between about 1:50 and about 1:1, between about 1:50 and about 1:2, between about 1:50 and about 1:5, or between about 1:50 and about 1:10, by mole. In certain embodiments, the ratio can be between about 1:30 and about 1:1, between about 1:30 and about 1:2, between about 1:30 and about 1:5, between about 1:30 and about 1:10, between about 1:20 and about 1:1, between about 1:20 and about 1:2, or between about 1:20 and about 1:5, by mole. In certain embodiments, the ratio can be between about 1:15 and about 1:1, between about 1:15 and about 1:2, between about 1:15 and about 1:5, between about 1:10 and about 1:1, between about 1:10 and about 1:2, between about 1:10 and about 1:5, between about 1:5 and about 1:1, or between about 1:5 and about 1:2, e.g., about 1:12 or about 1:6, by mole.

The amount of trigeminal-stimulating compound(s) in the air-space experienced by a user can also be expressed as a percentage of the overall quantity of fragrance compounds in the air-space, including additional fragrance compounds. By way of non-limiting example, the amount of trigeminal-stimulating compound(s) in the air-space experienced by a user can be between about 1% and about 50%, between about 1% and about 30%, between about 1% and about 20%, between about 1% and about 10%, between about 1% and about 5%, between about 1% and about 3% by mole. In certain embodiments, the amount can be between about 3% and about 50%, between about 3% and about 30%, between about 3% and about 20%, between about 3% and about 10% by mole. In certain embodiments, the amount can be between about 5% and about 50%, between about 5% and about 30%, between about 5% and about 20%, between about 5% and about 10% by mole. In certain embodiments, the amount can be between about 8% and about 15% by mole. In certain embodiments, the amount can be between about 10% and about 50%, between about 10% and about 30%, between about 10% and about 20% by mole. In certain embodiments, the amount can be between about 20% and about 50%, between about 20% and about 30%, or between about 30% and about 50% of the overall quantity of fragrance compounds in the air-space, by mole. The amount of trigeminal-stimulating compound(s) in the air-space experienced by a user can be influenced by the choice of support materials and the vapor pressure and boiling point of the trigeminal-stimulating compound(s) used.

In certain embodiments, the presently disclosed fragrance compositions and combinations can be incorporated into fragrance products and applications. The compositions and combinations of the presently disclosed subject matter can be used to impart improved olfactory effects to consumers in various products, including but not limited to aerosol air freshening products, gel air freshening products, candles, fragranced wax melts, potpourri, piezo-electric fragrancing devices, reed diffusers, fabrics, liquid electrical air fresheners, powered evaporative air fresheners, filter papers, laminated cardboard, membrane diffusers, ceramic diffusers, spray refresheners, and the like. The compositions and combinations of the presently disclosed subject matter are suitable for use in any device having a single or dual fragrance capability. For example, U.S. Pat. No. 8,695,891 discloses a dual fragrance delivery device. Examples of delivery devices are also disclosed in U.S. Publication No. 2012/0312893, U.S. Publication No. 2014/0048614, U.S. Pat. No. 8,833,366, and U.S. Pat. No. 8,603,963, the contents of each of which are hereby incorporated by reference in their entireties.

In certain embodiments, the presently disclosed fragrance compositions and combinations can be incorporated into consumer products including, but are not limited to, household or home care products. Non-limiting examples of such products include home cleaning products (e.g., hand and auto dish cleaners, hard surface cleaners, laundry products such as laundry detergents, softeners, cleaners, dryer sheets, etc.); pet care products (e.g., cat litter); sanitary products (e.g., towels, toilet paper, tissue paper, wet tissue paper, handkerchiefs, wet towels, etc.); writing products (e.g., pens, crayons, paints, pencils, paper, origami, seals, etc.); auto care products (e.g., cleaners, air fresheners, wipes, soaps, etc.); products for play (e.g., balls, beanbags, cards, tops, dolls, building blocks, etc.).

General purpose cleaners include, but are not limited to floor cleaners and carpet cleaners. Cleaners can be in several forms: isotropic liquids, thickened liquids with or without abrasive, pastes, gels, foams or sprays. In certain embodiments, they can be used directly from the bottle or after dilution in water. Various delivery methods have been devised for the convenience of the users, some are sprayed onto surfaces from trigger spray bottles, or alternatively they can be poured directly onto surfaces. General purpose cleaners can also contain additional ingredients such as acids for limescale removal, biocides for hygiene, or bleaching agents. For a standard floor cleaner composition see Surfactant Science Series Vol. 67 Liquid Detergents, chapter on Speciality Liquid Household Surface Cleaners p. 479, Table 4, the contents of which is hereby incorporated by reference in its entirety.

In certain embodiments, the presently disclosed fragrance compositions and combinations can be incorporated into bathroom cleaning products, including but not limited to, bath or tile cleaner, toilet bowl cleaner, sink cleaner, disinfectants, antimicrobial products, mildew cleaners, etc. In a non-limited example, bathroom cleaning products can include a solid of liquid toilet rim block. Solid or liquid toilet rim blocks are intended to be located under the rim of a lavatory bowl or urinal such that, during a flushing cycle, water from the cistern flows over the block, thereby dissolving a portion of the toilet rim block. In certain embodiments, rim blocks are cageless rim blocks which adhere directly to the surface of the lavatory pan, or solid toilet rim blocks which are placed in the cistern and dissolve slowly in the water contained therein. The solubility characteristics of these two products are quite different, since one is constantly under water while the other has intermittent short term contact with water. However, in certain embodiments, they both can contain a surfactant, fillers, bleaching agents, germicides and anti-limescale agents, and a fragrance composition as disclosed herein. Example formulations are described in EP 0 462 643, GB 2 178 442 and U.S. Pat. No. 4,874,536, the contents of each of which are hereby incorporated by reference in their entireties.

The liquid toilet rim blocks are devices that dispense liquid compositions directly into a lavatory bowl from under the rim of said bowl. Such liquid toilet rim blocks are usually attached by various means, such as hooks and the like, to the rim of the lavatory bowl. Every time a toilet equipped with a liquid toilet rim block is flushed, an amount of composition is dispensed into the lavatory bowl. Examples of liquid toilet rim blocks are given in WO 02/40792, EP 0 775 741 and WO 01/94520, which are incorporated herein by reference.

In certain embodiments, products include oral products such as pharmaceuticals (e.g., plasters, ointments, lotions, liniments, decongestants, cough mixtures, throat lozenges, indigestion preparations and oral analgesics, etc.); and others (e.g., tooth paste, tooth gel, oral wash, mouth rinse, mouthwash, flavoring, seasonings, chewing gum, etc.).

In certain embodiments, products include those applied to or brought into contact with a consumer's skin and body heat. These products can have an enhanced biomediated performance when applied. Products include fine fragrance (e.g., cologne, perfume, body sprays); personal care products (e.g., lotions, creams, body washes, hand soaps, shampoos, conditioners, soaps, deodorants, antiperspirants, etc.); cosmetics (e.g., skin cream, cleansing cream, night cream, hand cream, lotion, after-shave lotion, shaving creams, gels and foams, body lotion, foundation, lip stick, lip cream, nail polish, nail polish remover, talcum powder, anti-wrinkle and/or anti-aging cosmetics, sun protection products, sunburn lotions, massage oil, etc.); hair cosmetics (e.g., shampoo, rinse, conditioner, rinse in shampoo; hair styling agents such as pomade, hair tonic, hair gel, hair cream and hair mousse; hair growing agents; hair coloring agents; etc.); and bath agents (e.g., powder bath additives, solid foaming bath additives, bath oils, bubble bath aroma generators, bath salts, etc.).

In certain embodiments, the presently disclosed fragrance compositions and combinations can be incorporated into consumer products and provide a method for improving intensity, noticeability and perception thresholds. In other embodiments, the method can improve intensity, noticeability and perception thresholds of a fragrance composition over a 7-day period. In other embodiments, the method can improve intensity, noticeability and perception thresholds of a fragrance composition over a 14-day period.

As embodied in the Examples presented below, fragrance compositions and combinations of the presently disclosed subject matter can have advantages over other fragrance compositions and combinations. Fragrance compositions and combinations of the presently disclosed subject matter that include trigeminal-stimulating compounds can deliver an improved olfactory preference and liking as compared to similar compositions that do not include the trigeminal-stimulating compounds. Fragrance compositions and combinations that include trigeminal-stimulating compounds can deliver a heightened (increased) odor intensity as compared to similar compositions that do not include the trigeminal-stimulating compounds. Fragrance compositions and combinations that include trigeminal-stimulating compounds can provide increased long-term noticeability of the fragrance as compared to similar compositions that do not include the trigeminal-stimulating compounds. Long term-noticeability can be measured as the intensity of a fragrance over time. Fragrances whose intensity decreases more gradually have greater long-term noticeability. Fragrance compositions and combinations that include trigeminal-stimulating compounds can provide lower odor perception thresholds to users, allowing the fragrance to be perceived at a greater distance from its source as compared to similar compositions that do not include the trigeminal-stimulating compounds. Fragrance compositions and combinations that include trigeminal-stimulating compounds can provide decreased adaptation and habituation to the fragrance as compared to similar compositions that do not include the trigeminal-stimulating compounds. That is, users can, over time, retain greater sensitivity to and awareness of fragrance compositions and combinations that include trigeminal-stimulating compounds as compared to similar compositions that do not include the trigeminal-stimulating compounds.

EXAMPLES

The presently disclosed subject matter will be better understood by reference to the following Examples, which are provided as exemplary of the invention, and not by way of limitation. Abbreviations have the usual meaning in the art. COOLACT® and HOTACT® are registered trademarks of Takasago International Corporation.

The liking and intensity scores presented below are averaged results obtained from testing with blind panels of expert testers. Panelists scored fragrances for liking and intensity on a 15-point scale, with higher scores representing fragrances that were more preferred (liking) or stronger (intensity).

Example 1

Fragrance Combination

The following test was run in 800 ft$^3$ olfactory booths which are typically used for olfactory testing. In Booth A (control) were placed two electric air freshening units, one unit filled with a tropical/vanilla fragrance composition and the other filled with 100% dipropylene glycol. The tropical/vanilla fragrance composition contained 50% fragrance compounds and 50% solvent, by weight. In each of ten (10) booths (Booths B1-B10) were placed two electric air freshening units, one unit filled with the same tropical/vanilla fragrance and the other filled with a composition containing one or more trigeminal-stimulating compounds. The compositions containing one or more trigeminal-stimulating compounds are presented in Table 1 (Formulae 1-10). The composition of Formula 1 was placed in Booth B1; the composition of Formula 2 was placed in Booth B2; and so on.

TABLE 1

| | component concentration (weight %) | | | |
|---|---|---|---|---|
| | l-menthol | COOLACT® 38D | HOTACT® VEE | dipropylene glycol |
| Formula 1 | 30 | 0 | 0 | 70 |
| Formula 2 | 20 | 5 | 5 | 70 |
| Formula 3 | 15 | 15 | 0 | 70 |
| Formula 4 | 15 | 0 | 15 | 70 |
| Formula 5 | 0 | 30 | 0 | 70 |
| Formula 6 | 5 | 20 | 5 | 70 |
| Formula 7 | 10 | 10 | 10 | 70 |
| Formula 8 | 0 | 15 | 15 | 70 |
| Formula 9 | 0 | 0 | 30 | 70 |
| Formula 10 | 5 | 5 | 20 | 70 |

All of the electric units were powered up and allowed to equilibrate in the booths for 1 hour. 26 trained panelists were asked to spend two minutes in a booth, followed by a one minute rest period outside the booths, then move on to the next booth. The order in which the booths were experienced was randomized for each panelist. The panelists were then asked to rate their experience on a scale of 1-15 for their overall liking of the fragrance and the overall intensity of the fragrance for each booth. The results, averaged over all panelists, are presented in Table 2.

TABLE 2

| | Overall liking | Overall intensity |
|---|---|---|
| Booth A (Control) | 7.3 | 7.9 |
| Booth B1 (Formula 1) | 6.9 | 8.6 |
| Booth B2 (Formula 2) | 7.7 | 8.5 |
| Booth B3 (Formula 3) | 8.2 | 9.0 |
| Booth B4 (Formula 4) | 8.2 | 8.9 |
| Booth B5 (Formula 5) | 7.4 | 8.0 |
| Booth B6 (Formula 6) | 7.8 | 8.1 |
| Booth B7 (Formula 7) | 7.7 | 8.4 |
| Booth B8 (Formula 8) | 7.9 | 7.7 |
| Booth B9 (Formula 9) | 7.4 | 8.4 |
| Booth B10 (Formula 10) | 7.6 | 8.2 |

As shown in Table 2, the fragrance combinations that included trigeminal-stimulating compounds (placed in Booths B1-B10) generally had improved overall liking and overall intensity scores as compared to the control (placed in Booth A). For example, combination of the tropical/vanilla fragrance with compositions of Formulae 2, 3, 4, 5, 6, 7, 9, and 10 had improved scores for both liking and intensity as compared to the control.

Example 2

Fragrance Combination

The following test was run in 800 ft$^3$ olfactory booths which are typically used for olfactory testing. In Booth C (control) were placed two electric air freshening units, one unit filled with a fruity/tropical fragrance and the other filled with 100% dipropylene glycol. The fruity/tropical fragrance composition contained 50% fragrance compounds and 50% solvent, by weight. In each of ten (10) booths (Booths D1-D10) were placed two electric air freshening units, one unit filled with the same fruity/tropical fragrance and the other filled with a composition containing one or more trigeminal-stimulating compounds. The compositions containing one or more trigeminal-stimulating compounds are presented in Table 3 (Formulae 1-10). The composition of Formula 1 was placed in Booth D1; the composition of Formula 2 was placed in Booth D2; and so on.

TABLE 3

| | component concentration (weight %) | | | |
|---|---|---|---|---|
| | l-menthol | COOLACT® 38D | HOTACT® VEE | dipropylene glycol |
| Formula 1 | 30 | 0 | 0 | 70 |
| Formula 2 | 20 | 5 | 5 | 70 |
| Formula 3 | 15 | 15 | 0 | 70 |
| Formula 4 | 15 | 0 | 15 | 70 |
| Formula 5 | 0 | 30 | 0 | 70 |
| Formula 6 | 5 | 20 | 5 | 70 |
| Formula 7 | 10 | 10 | 10 | 70 |
| Formula 8 | 0 | 15 | 15 | 70 |
| Formula 9 | 0 | 0 | 30 | 70 |
| Formula 10 | 5 | 5 | 20 | 70 |

All of the electric units were powered up and allowed equilibrate in the booths for 1 hour. 30 trained panelists were asked to spend two minutes in a booth, followed by a one minute rest period outside the booths, then move on to the next booth. The order in which the booths were experienced was randomized for each panelist. The panelists were then asked to rate their experience on a scale of 1-15 for their overall liking of the fragrance and the overall intensity of the fragrance for each booth. The results, averaged over all panelists, are presented in Table 4.

TABLE 4

| | Overall liking | Overall intensity |
|---|---|---|
| Booth C (Control) | 9.3 | 9.8 |
| Booth D1 (Formula 1) | 9.2 | 10.4 |
| Booth D2 (Formula 2) | 9.1 | 10.7 |
| Booth D3 (Formula 3) | 11.0 | 10.7 |
| Booth D4 (Formula 4) | 9.7 | 9.7 |
| Booth D5 (Formula 5) | 9.8 | 9.5 |
| Booth D6 (Formula 6) | 9.6 | 10.7 |
| Booth D7 (Formula 7) | 9.0 | 8.4 |
| Booth D8 (Formula 8) | 10.3 | 9.9 |
| Booth D9 (Formula 9) | 10.0 | 10.3 |
| Booth D10 (Formula 10) | 7.6 | 9.1 |

As shown in Table 4, the fragrance combinations that included trigeminal-stimulating compounds (placed in Booths D1-D10) had improved overall liking and overall intensity scores as compared to the control (placed in Booth C). For example, combination of the fruity/tropical fragrance with compositions of Formulae 3, 6, 8, and 9 had improved scores for both liking and intensity as compared to the control.

Example 3

Fragrance Combination

The following test was run in 800 ft$^3$ olfactory booths which are typically used for olfactory testing. In Booth E (control) were placed two electric air freshening units, one unit filled with a green/floral fragrance and the other filled with 100% dipropylene glycol. The green/floral fragrance composition contained 50% fragrance compounds and 50% solvent, by weight. In each of ten (10) booths (Booths F1-F10) were placed two electric air freshening units, one unit filled with the same green/floral fragrance and the other filled with a composition containing one or more trigeminal-stimulating compounds. The compositions containing one or more trigeminal-stimulating compounds are presented in Table 5 (Formulae 1-10). The composition of Formula 1 was placed in Booth F1; the composition of Formula 2 was placed in Booth F2; and so on.

TABLE 5

| | component concentration (weight %) | | | |
|---|---|---|---|---|
| | l-menthol | COOLACT® 38D | HOTACT® VEE | dipropylene glycol |
| Formula 1 | 30 | 0 | 0 | 70 |
| Formula 2 | 20 | 5 | 5 | 70 |
| Formula 3 | 15 | 15 | 0 | 70 |
| Formula 4 | 15 | 0 | 15 | 70 |
| Formula 5 | 0 | 30 | 0 | 70 |
| Formula 6 | 5 | 20 | 5 | 70 |
| Formula 7 | 10 | 10 | 10 | 70 |
| Formula 8 | 0 | 15 | 15 | 70 |
| Formula 9 | 0 | 0 | 30 | 70 |
| Formula 10 | 5 | 5 | 20 | 70 |

All of the electric units were powered up and allowed to equilibrate in the booths for 1 hour. 36 trained panelists were asked to spend two minutes in a booth, followed by a one minute rest period outside the booths, then move on to the next booth. The order in which the booths were experienced was randomized for each panelist. The panelists were then asked to rate their experience on a scale of 1-15 for their overall liking of the fragrance and the overall intensity of the fragrance for each booth. The results, averaged over all panelists, are presented in Table 6.

TABLE 6

| | Overall liking | Overall intensity |
|---|---|---|
| Booth E (Control) | 8.3 | 9.1 |
| Booth F1 (Formula 1) | 8.7 | 10.0 |
| Booth F2 (Formula 2) | 8.5 | 9.6 |
| Booth F3 (Formula 3) | 8.6 | 9.8 |
| Booth F4 (Formula 4) | 7.7 | 9.6 |
| Booth F5 (Formula 5) | 8.4 | 10.6 |
| Booth F6 (Formula 6) | 8.6 | 9.9 |
| Booth F7 (Formula 7) | 8.3 | 9.5 |
| Booth F8 (Formula 8) | 8.4 | 9.7 |
| Booth F9 (Formula 9) | 8.4 | 9.6 |
| Booth F10 (Formula 10) | 8.3 | 8.3 |

As shown in Table 6, the fragrance combinations that included trigeminal-stimulating compounds (placed in Booths F1-F10) generally had improved overall liking and overall intensity scores as compared to the control (placed in Booth E). For example, combination of the green/floral fragrance with compositions of Formulae 1, 2, 3, 5, 6, 8, and 9 had improved scores for both liking and intensity as compared to the control.

Example 4

Fragrance Compositions

The following fragrance compositions containing one or more trigeminal-stimulating compounds are formulated as summarized in Table 7.

TABLE 7

| | 4A | 4B | 4C | 4D | 4E | 4F | 4G | 4H | 4I |
|---|---|---|---|---|---|---|---|---|---|
| Benzyl alcohol | 90.0% | — | — | — | — | — | — | — | — |
| Coolact® P | 9.7% | 10.0% | — | — | 30.0% | — | — | 29.5% | — |
| Hotact® VBE | 0.3% | — | — | 2.0% | — | — | 3.0% | — | — |
| Dowanol™ DPMA | — | 80.0% | — | — | — | — | — | — | 60.0% |
| L-menthol | — | 10.0% | — | — | 15.0% | — | — | — | 14.0% |
| Benzyl benzoate | — | — | 70.0% | — | — | — | — | — | — |
| Coolact® HK | — | — | 14.9% | — | — | — | — | — | — |
| Coolact® 38D | — | — | 14.9% | 13.0% | — | — | — | — | — |
| Capsicum oleoresin | — | — | 0.2% | — | — | — | — | — | — |
| Dipropylene glycol | — | — | — | 60.0% | — | — | — | — | — |

TABLE 7-continued

| | | | | | | | | | |
|---|---|---|---|---|---|---|---|---|---|
| 1,8-cineole | — | — | — | 25.0% | — | — | — | — | — |
| Ethanol | — | — | — | — | 50.0% | — | — | — | — |
| Hotact ® VEE | — | — | — | — | 4.5% | 2.5% | — | — | 1.0% |
| Spilanthol | — | — | — | — | 0.5% | — | — | 0.5% | — |
| Peppermint oil | — | — | — | — | — | 97.5% | 95.0% | — | 25.0% |
| Jambu oleoresin | — | — | — | — | — | — | 2.0% | — | — |
| Orange Terpenes | — | — | — | — | — | — | — | 70.0% | — |
| black pepper extract | — | — | — | — | — | — | — | — | — |
| Spearmint oil | — | — | — | — | — | — | — | — | — |
| Total | 100.0% | 100.0% | 100.0% | 100.0% | 100.0% | 100.0% | 100.0% | 100.0% | 100.0% |

| | | 4J | 4K | 4L | 4M | 4N | 4O | 4P |
|---|---|---|---|---|---|---|---|---|
| | Benzyl alcohol | 15.0% | — | — | — | — | — | — |
| | Coolact ® P | — | — | — | — | — | — | — |
| | Hotact ® VBE | — | — | — | — | — | — | — |
| | Dowanol ™ DPMA | — | — | — | — | — | — | — |
| | L-menthol | 25.0% | — | — | — | 5.0% | 15.0% | 14.5% |
| | Benzyl benzoate | — | — | — | 64.0% | — | — | — |
| | Coolact ® HK | 22.0% | — | 15.0% | — | — | — | — |
| | Coolact ® 38D | — | — | — | — | — | 15.0% | 14.5% |
| | *Capsicum* oleoresin | — | — | — | — | 1.0% | — | — |
| | Dipropylene glycol | — | — | — | — | 93.5% | 69.85% | 70% |
| | 1,8-cineole | — | — | — | — | — | — | — |
| | Ethanol | — | — | 80.0% | — | — | — | — |
| | Hotact ® VEE | — | 1.0% | 5.0% | — | — | 0.15% | 1% |
| | Spilanthol | — | 0.5% | — | — | 0.5% | — | — |
| | Peppermint oil | — | 98.5% | — | — | — | — | — |
| | Jambu oleoresin | — | — | — | 1.0% | — | — | — |
| | Orange Terpenes | 35.0% | — | — | — | — | — | — |
| | black pepper extract | 3.0% | — | — | — | — | — | — |
| | Spearmint oil | — | — | — | 35.0% | — | — | — |
| | Total | 100.0% | 100.0% | 100.0% | 100.0% | 100.0% | 100.0% | 100.0% |

Example 5

Fragrance Combination

The following test was run by 5 expert panelists in their homes. At the beginning of the test, each panelist plugged in a electric air freshening unit filled with a tropical/vanilla fragrance and evaluated the intensity of the fragrance at a point 6 feet away from the unit each day. The tropical/vanilla fragrance composition contained 50% fragrance compounds and 50% solvent, by weight. Intensities were rated on a scale of 1-15. After 7 days, while leaving the first electric unit plugged in, each panelist plugged in a second electric air freshening unit in close proximity to the existing unit, filled with a composition 4P as described in Table 7.

The panelists continued to take daily intensity ratings at a point 6 feet away from the units. The results are presented in Table 8.

TABLE 8

| | Intensity score |
|---|---|
| Day 1 | 8.9 |
| Day 2 | 7.8 |
| Day 3 | 8.4 |
| Day 4 | 8.1 |
| Day 5 | 7.4 |
| Day 6 | 6.4 |
| Day 7 | 5.0 |
| Day 8 (introduction of trigeminal-stimulating compounds) | 4.1 |
| Day 9 | 4.0 |
| Day 10 | 4.5 |
| Day 11 | 5.8 |

TABLE 8-continued

|  | Intensity score |
|---|---|
| Day 12 | 5.1 |
| Day 13 | 3.2 |
| Day 14 | 3.5 |

As expected, a typical normal intensity decay from habituation to the fragrance was displayed from days 1-7. Surprisingly, upon introduction of the composition that included trigeminal-stimulating compounds, a secondary maximum of intensity was experienced around day 11. Thus, introduction of trigeminal-stimulating compounds into a fragrance combination heightened the long-lasting perception of the fragrance to the user.

Example 6

Herbaceous-Gourmand Fragrances

The following test was run in olfactory booths which are typically used for olfactory testing. In Booth A (control) was placed one electric air freshening unit, filled with a herbaceous-gourmand fragrance. In each of eight (8) booths (Booths 1-8) were placed one of two electric air freshening units, one unit filled with an herbaceous-gourmand fragrance and of a mixture of trigeminal-stimulating compounds (TSC) (present at 10.1% w/w of the total composition) ("6A") and the other filled with an herbaceous-gourmand fragrance and of the same mixture of trigeminal-stimulating compounds (present at 6.5% w/w of the total composition) ("6B"). The TSC mixture comprised L-menthol, Coolact® 38D and Hotact® VEE in a ratio of 1:1:.01.

All of the electric units were powered up and allowed equilibrate in the booths for 20 minutes. 24 female, semi-trained panelists (aged 24-54) were asked to spend 72 minutes in a booth, once a day, for three days. The panelists visited the same booth for each session. Methods of measuring perceived intensity were employed, including the use of LMS. The LMS data is shown below in Table 9. The panelists were asked to rate their overall liking of the fragrance on a scale of 1-9. The data is shown below in Table 10. The panelists were immersed in the booth with no noise or distractions. They were asked to answer questions using sensory software every 4 minutes. The findings are summarized in FIG. 1 and Tables 9-10.

TABLE 9

| Perceived Intensity | | | |
|---|---|---|---|
|  | Control | 6A | 6B |
| 0-12 min LMS | 1.35 | 1.35 | 1.33 |
| 13-24 min LMS | 1.29 | 1.24 | 1.21 |
| 25-36 min LMS | 1.23 | 1.25 | 1.22 |
| 37-48 min LMS | 1.21 | 1.21 | 1.22 |
| 49-60 min LMS | 1.19 | 1.18 | 1.16 |
| 64-72 min LMS | 1.13 | 1.17 | 1.14 |

Average Log Labeled Magnitude Scale Scores (0 = no scent, 2 = strongest imaginable)
* significantly higher than control 80% LOC,
** significantly higher than Control 90% LOC,
*** significantly higher than control 95% LOC, 2 tailed testing within subjects

TABLE 10

| Hedonics (Scale = 1-9) | | | |
|---|---|---|---|
|  | Control | 6A | 6B |
| Liking 0-12 min | 6.28 | 6.63 | 6.65 |
| Liking 13-24 min | 5.93 | 6.54 | 6.19 |
| Liking 25-36 min | 5.67 | 6.43** | 6.25* |
| Liking 37-48 min | 5.68 | 6.29* | 5.93 |
| Liking 49-60 min | 5.53 | 6.22* | 5.99 |
| Liking 64-72 min | 5.37 | 6.26** | 6.10** |

*significantly higher than control 80% LOC,
**significantly higher than Control 90% LOC,
*** significantly higher than control 95% LOC, 2 tailed testing within subjects As shown in FIG. 1a, Formulation 6A including TSC provoked consistently higher ratings, and maintained ratings over 6.0 (a typical cutoff value of acceptablity in consumer product applications) for the entire duration of time as compared to the control, and provoked a slower rate of decay in hedonics overall. This was accomplished without significantly altering the strength perception of the fragrance.

Figure 1B:
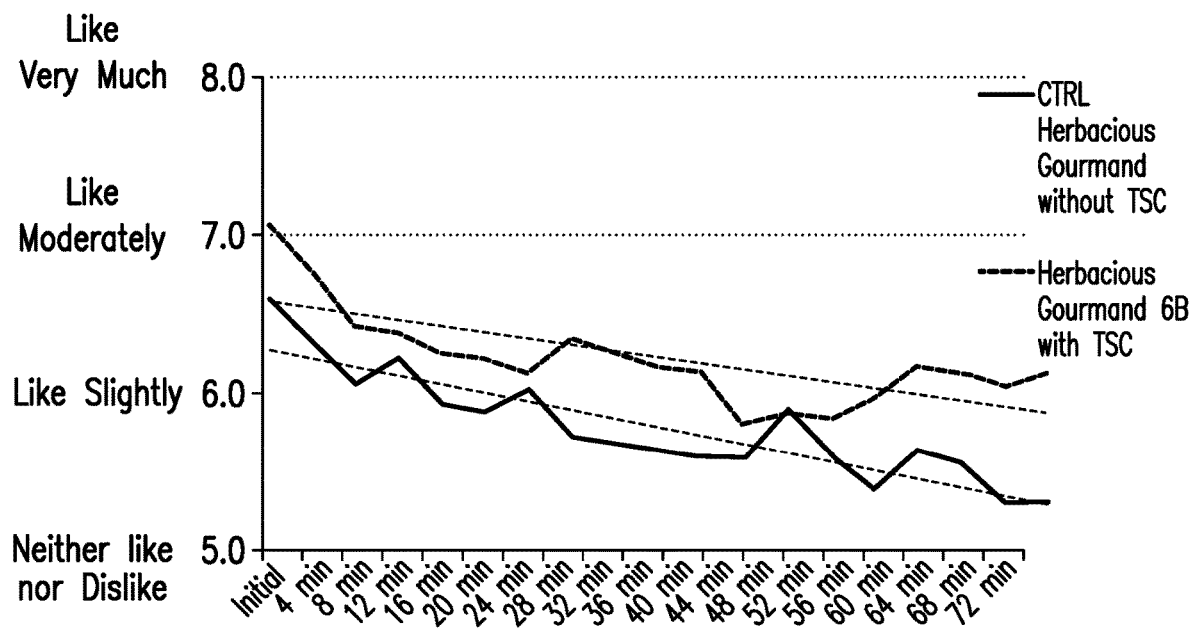

As shown in FIG. 1b, Formulation 6B including TSC provoked consistently higher ratings, and maintained ratings over 6.0 (a typical cutoff value of acceptablity in consumer product applications) for a substantially greater duration of time as compared to the control.

Example 7

Clean/Laundry Fragrances

The following tests using clean/laundry fragrances combined with TSC were run in olfactory booths which are typically used for olfactory testing.

Booth conditions were established: 1 comprising an electric air freshening unit filled with a clean fragrance; 1 comprising an electric air freshening unit filled with a clean fragrance with the TSC mixture of Example 6 present in an amount of 8.4% w/w of the total composition. In each of eight (8) booths (Booths 1-8) were placed one of the electric air freshening units.

All of the electric units were powered up and allowed equilibrate in the booths for 20 minutes. 24 female semi-trained panelists (aged 24-54) were asked to spend 72 minutes in a booth, once a day, for four days. The panelists visited the same booth for each session. Methods of measuring perceived intensity were employed, including the use of LMS. The LMS data is shown below in Table 11. The panelists were asked to rate their overall liking of the fragrance on a scale of 1-9. The data is shown below in Table 12. The panelists were immersed in the booth with no noise or distractions. They were asked to answer questions using sensory software every 4 minutes. The findings are summarized in FIG. 2 and Tables 11-12.

TABLE 11

| Intensity | | |
|---|---|---|
|  | Clean | Clean (with 8.4% TSC) |
| 0-12 min LMS | 1.33 | 1.39 |
| 13-24 min LMS | 1.26 | 1.34 |
| 25-36 min LMS | 1.27 | 1.31 |
| 37-48 min LMS | 1.24 | 1.27 |

TABLE 11-continued

Intensity

|  | Clean | Clean (with 8.4% TSC) |
|---|---|---|
| 49-60 min LMS | 1.23 | 1.21 |
| 64-72 min LMS | 1.26 | 1.23 |

Average Log Labeled Magnitude Scale Scores (0 = no scent, 2 = strongest imaginable)
* significantly higher than control 80% LOC,
** significantly higher than Control 90% LOC,
*** significantly higher than control 95% LOC, 2 tailed testing within subjects.

TABLE 12

Hedonics (Scale = 1-9)

|  | Clean | Clean (with 8.4% TSC) |
|---|---|---|
| Liking 0-12 min | 6.09 | 6.61* |
| Liking 13-24 | 5.88 | 6.32** |
| Liking 25-36 | 5.79 | 6.24* |
| Liking 37-48 | 5.83 | 6.13 |
| Liking 49-60 | 5.72 | 6.15 |
| Liking 64-72 | 5.76 | 6.18 |

Average Liking Scores (1 = dislike extremely, 9 = like extremely)
*significantly higher than control 80% LOC,
**significantly higher than Control 90% LOC,
*** significantly higher than control 95% LOC, 2 tailed testing within subjects.

Figure 2:
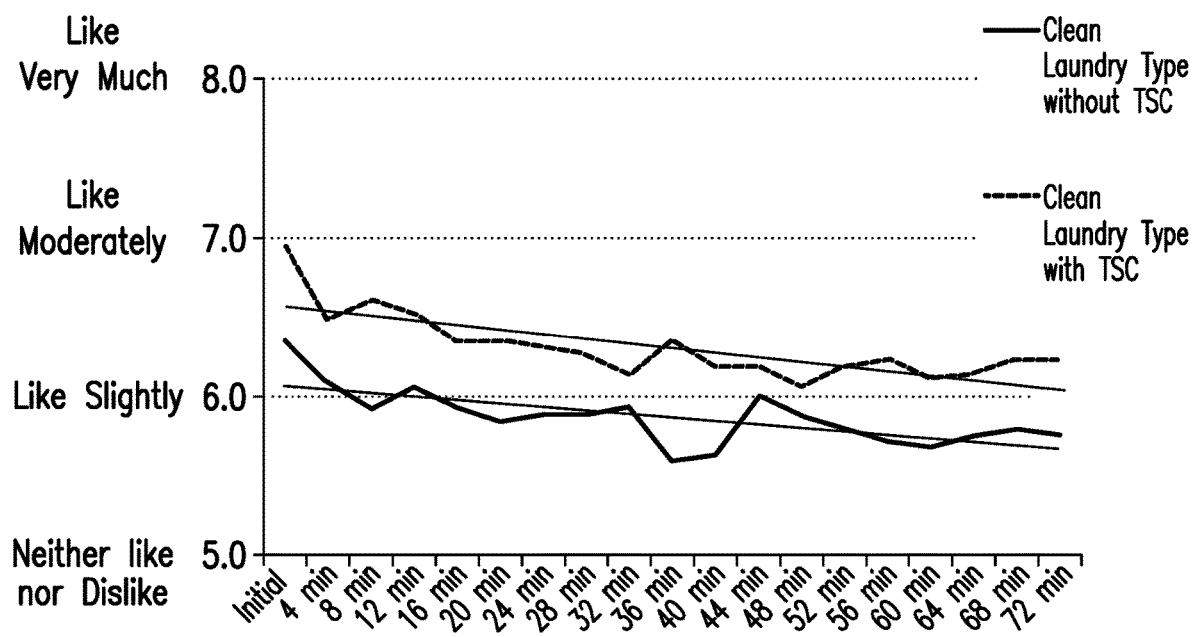
FIG. 2 depicts the results of Example 7. The hedonics (or overall liking) are measured on a scale of 1-9 over 72 minutes.

As shown in FIG. 2, the TSC containing formulation provoked consistently higher ratings and maintained ratings over 6.0 (a typical cutoff value of acceptablity in consumer product applications) for the entire duration of time as compared to the control. The TSC containing formulation also provoked a slower rate of decay in hedonics overall. This was accomplished without significantly altering the strength perception of the fragrance.

Example 8

Fruity Fragrances

Booth conditions were established: 1 comprising an electric air freshening unit filled with a fruity fragrance; 1 comprising an electric air freshening unit filled with a fruity fragrance with the TSC mixture of Example 6 present in an amount of 7.0% w/w of the total composition. In each of eight (8) booths (Booths 1-8) were placed one of the electric air freshening units. The test was run as described in Example 7. Methods of measuring perceived intensity were employed, including the use of LMS. The LMS data is shown below in Table 13. The panelists were asked to rate their overall liking of the fragrance on a scale of 1-9. The data is shown below in Table 14. The findings are summarized in FIG. 3 and Tables 13-14.

TABLE 13

Intensity

|  | Fruity | Fruity (with 7.0% TSC) |
|---|---|---|
| 0-12 min LMS | 1.53 | 1.48 |
| 13-24 min LMS | 1.47 | 1.41 |
| 25-36 min LMS | 1.42 | 1.39 |
| 37-48 min LMS | 1.37 | 1.37 |

TABLE 13-continued

Intensity

|  | Fruity | Fruity (with 7.0% TSC) |
|---|---|---|
| 49-60 min LMS | 1.27 | 1.35 |
| 64-72 min LMS | 1.24 | 1.30 |

Average Log Labeled Magnitude Scale Scores (0 = no scent, 2 = strongest imaginable)
* significantly higher than control 80% LOC,
** significantly higher than Control 90% LOC,
*** significantly higher than control 95% LOC, 2 tailed testing within subjects

TABLE 14

Hedonics (Scale = 1-9)

|  | Fruity | Fruity (with 7.0% TSC) |
|---|---|---|
| Liking 0-12 min | 7.43 | 7.21 |
| Liking 13-24 | 7.06 | 7.04 |
| Liking 25-36 | 6.99 | 6.96 |
| Liking 37-48 | 6.72 | 6.93 |
| Liking 49-60 | 6.61 | 6.92 |
| Liking 64-72 | 6.53 | 6.82 |

Average Liking Scores (1 = dislike extremely, 9 = like extremely)
* significantly higher than control 80% LOC,
** significantly higher than Control 90% LOC,
*** significantly higher than control 95% LOC, 2 tailed testing within subjects.

Figure 3:
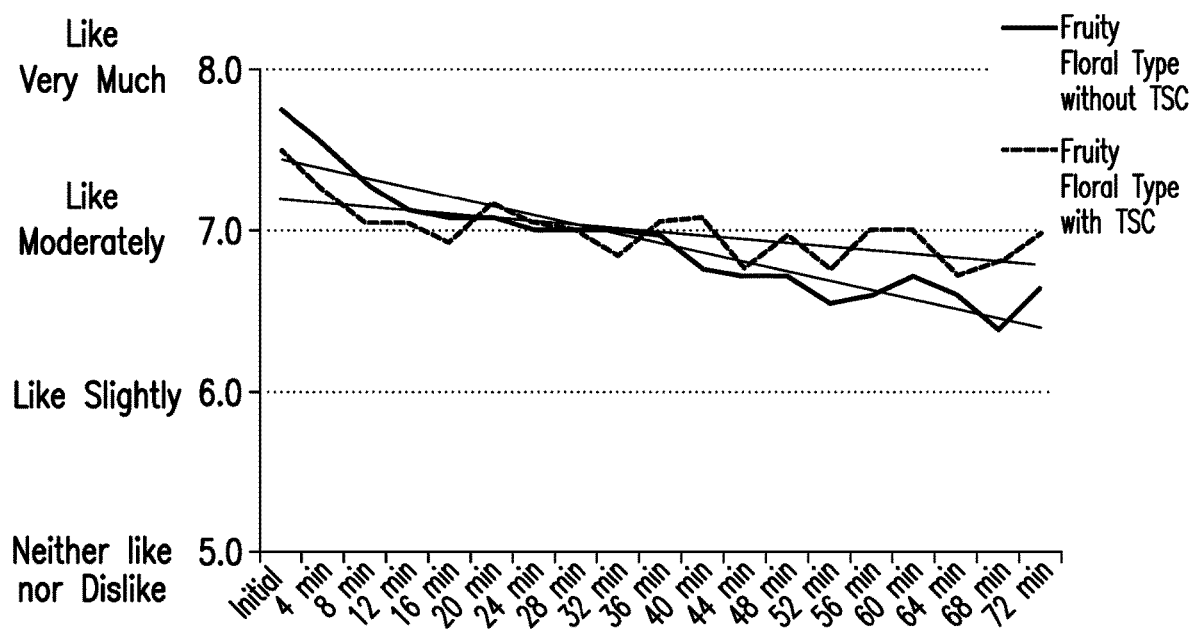
FIG. 3 depicts the results of Example 8. The hedonics (or overall liking) are measured on a scale of 1-9 over 72 minutes.

As shown in FIG. 3, the TSC containing fruity formulation provoked consistently higher ratings after the initial 12 minutes and maintained ratings over 6.0 (a typical cutoff value of acceptablity in consumer product applications) for the entire duration of time as compared to the control. The TSC containing formulation also provoked a slower rate of decay in hedonics overall. This was accomplished without significantly altering the strength perception of the fragrance.

Example 9

Fragrance Combination

The following test was run in 800 ft³ olfactory booths which are typically used for olfactory testing. In a control booth two electric air freshening units were placed, one unit filled with a herbaceous-gourmand fragrance and the other filled with 100% dipropylene glycol. In each of eight (8) booths were placed two electric air freshening units, one unit filled with an herbaceous-gourmand fragrance and the other filled with a composition containing a TSC mixture as described by 4O in Table 7.

Figure 4:
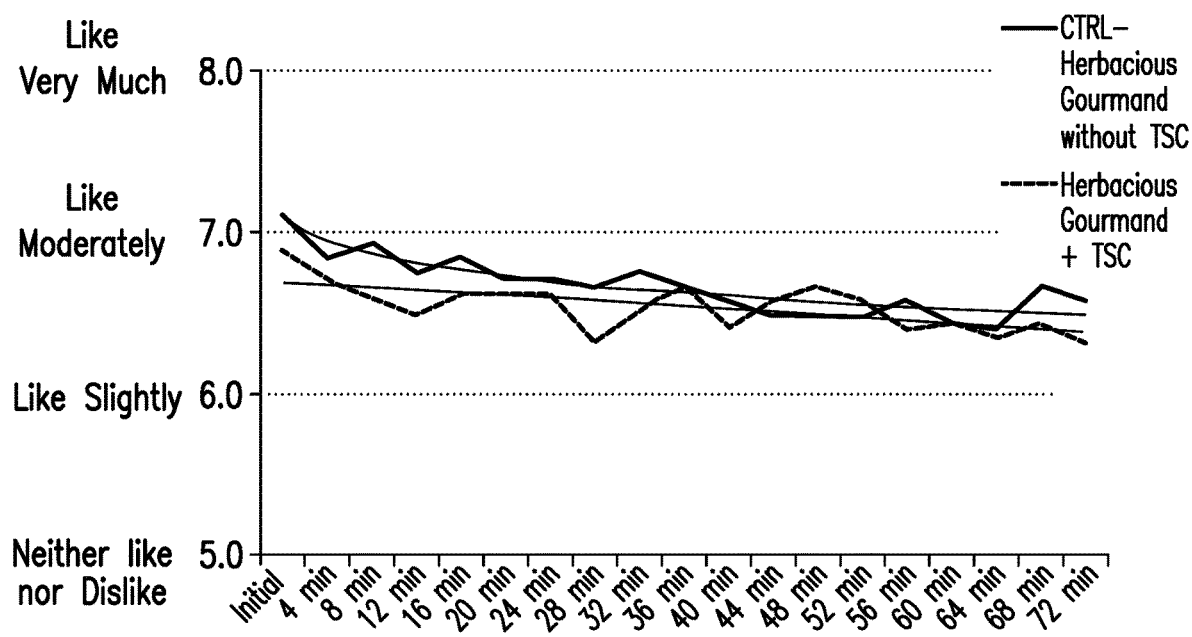
FIG. 4 depicts the results of Example 9. The hedonics (or overall liking) are measured on a scale of 1-9 over 72 minutes.

All of the electric units were powered up and allowed to equilibrate in the booths for 20 minutes. The electric unit comprising the TSC mixture was programed to control the rate of release and provided 15.8% TSC to the booth airspace. 22 trained panelists were asked to spend 72 solitary minutes in a booth, with no noises or distractions once a day, for three days. The panelists visited the same booth for each session. Methods of measuring perceived intensity were employed, including the use of LMS. The LMS data is shown below in Table 15. The panelists were asked to rate their overall liking of the fragrance on a scale of 1-9. The data is shown below in Table 16. They were asked to answer questions using sensory software every 4 minutes. The findings are summarized in FIG. 4 and Tables 15-16.

TABLE 15

Intensity Labeled Magnitude Scale.

|  | Control | herbaceous-gourmand fragrance + 15.8% TSC |
|---|---|---|
| LMS 0-12 min | 1.33 | 1.36 |
| LMS 13-24 | 1.29 | 1.32 |
| LMS 25-36 | 1.27 | 1.32 |
| LMS 37-48 | 1.22 | 1.32* |
| LMS 49-60 | 1.21 | 1.32* |
| LMS 64-72 | 1.21 | 1.28 |

Average Log Labeled Magnitude Scale Scores (0 = no scent, 2 = strongest imaginable)
*significantly higher than control 80% LOC,
** significantly higher than Control 90% LOC,
*** significantly higher than control 95% LOC, 2 tailed testing within subjects

TABLE 16

Hedonics

|  | Control | herbaceous-gourmand fragrance + 15.8% TSC |
|---|---|---|
| Liking 0-12 min | 6.98 | 6.73 |
| Liking 13-24 | 6.82 | 6.68 |
| Liking 25-36 | 6.76 | 6.56 |
| Liking 37-48 | 6.58 | 6.61 |
| Liking 49-60 | 6.56 | 6.53 |
| Liking 64-72 | 6.61 | 6.43 |

Average Liking Scores (1 = dislike extremely, 9 = like extremely)
* significantly higher than control 80% LOC,
** significantly higher than Control 90% LOC,
*** significantly higher than control 95% LOC, 2 tailed testing within subjects.

With regard to the overall liking of the product, addition of TSC decreased the initial hedonics of the fragrances. However, the addition of TSC successfully produced reduced decay slopes, such that there was little difference in panelists' overall opinion of the fragrance over the 72 minute period as compared to the control.

Example 10

Home Use (Herbacious-Gourmand)

In this Example, the formulations 6A and 6B, with and without TSC, tested in Example 6 were tested in the consumer's home.

The following tests were run inside a consumer's home over 28 days. Each consumer (N=50) was provided with two different plug-in air fresheners. The first air freshener was used for the first 14 days. The second air freshener was used for the second 14 days. The order of usage between control and the TSC containing products was randomized and counterbalanced for all cells. 24 hours after installing the first air freshener, the consumer was asked to fill out a short questionnaire including questions such as overall opinion of the product, what was specifically liked/disliked, how it compared to air fresheners the consumer typically uses, opinion of scent, how noticeable the scent was, how far away from the plug-in the fragrance still smelled, strength, and change in strength over time. The consumer filled out a substantially similar but longer questionnaire on day 7 and day 14. On day 14, the consumer exchanged the first plug-in for the second test plug-in and repeated the test. After evaluating both plug-ins the consumer was asked a series of questions comparing the first and second plug-ins.

Figure 5A:
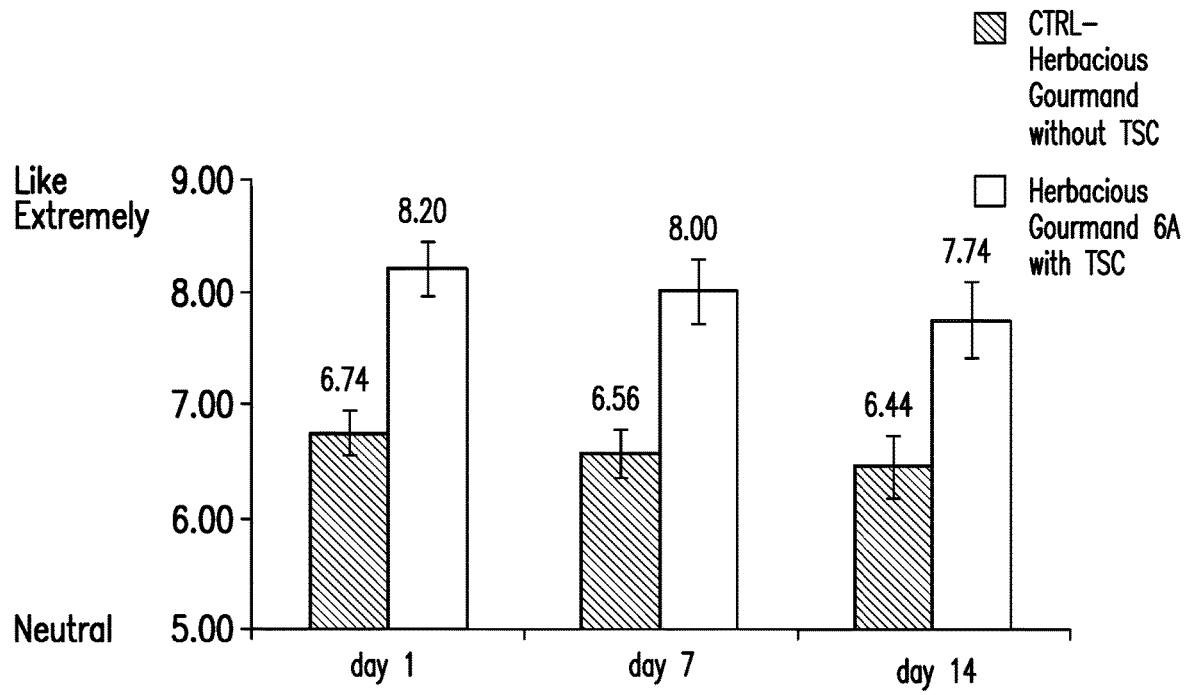
FIGS. 5a-5b depict the results of the home use test of Example 10.
Figure 5B:
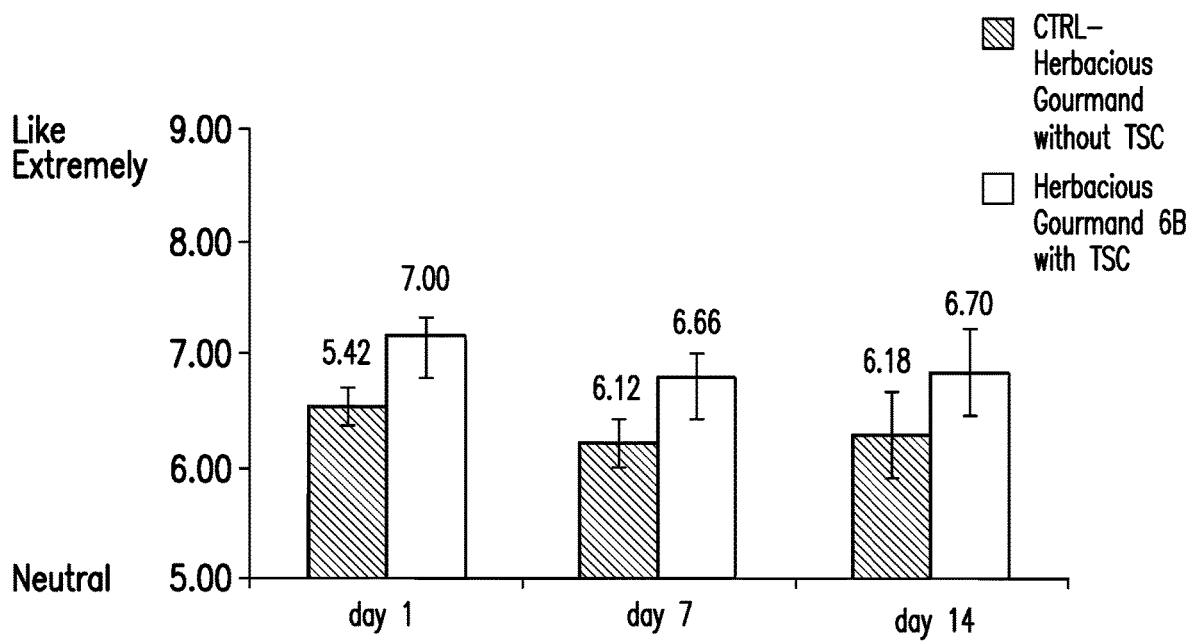

The overall opinion of fragrance over each 14 day period is illustrated in FIGS. 5a-b. Products containing TSC generated significantly higher liking scores among consumers across the span of the usage period. After using the products for 14 days, the consumers were asked additional preference questions comparing the control, 6A, and 6B. Consumers' responses to the questionnaire are summarized in FIG. 6a-f. These Figures illustrated that there is evidence that the addition of TSC to formulations 6A and 6B reduces hedonic fatigue/habituation and modulated a variety of emotive states.

Example 11

Home Use (Clean/Laundry)

In this Example, air fresheners with a clean/laundry type fragrance, with and without TSC, were tested in the consumers' homes (N=30).

The following tests were run inside a consumer's home over 14 days. Each consumer was provided with two different plug-in air fresheners. The first plugin was used for the first 7 days. The second plugin was used for the second 7 days. 24 hours after installing the first air freshener, the consumer was asked to fill out a questionnaire including questions such as overall opinion of the product, what was specifically liked/disliked, how it compared to air fresheners the consumer typically uses, opinion of scent, how noticeable the scent was, how far away from the plug-in the fragrance still smelled, strength, and change in strength over time. The consumer filled out a substantially similar questionnaire on day 7. On day 7, the consumer exchanged the first plug-in for the second test plug-in and repeated the test. After evaluating both plug-ins the consumer was asked a series of questions comparing the first and second plug-ins.

Figure 7:
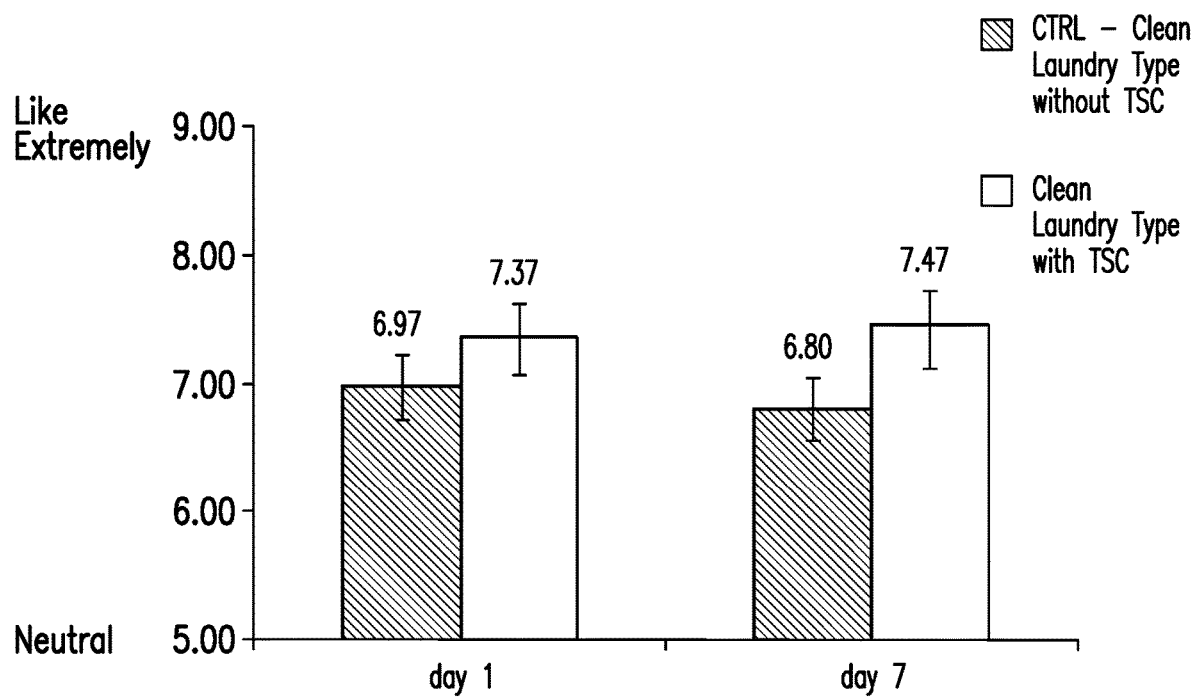
FIG. 7 depicts the results of the home use test of Example 11.

Results were collected on day 1 and day 7 of the home use test. FIG. 7 illustrates the overall opinion of the fragrance. The products containing TSC generated significantly higher liking scores at the 7 day time point than those that did not contain TSC.

Example 12

Home Use (Fruity/Floral)

Figure 8:
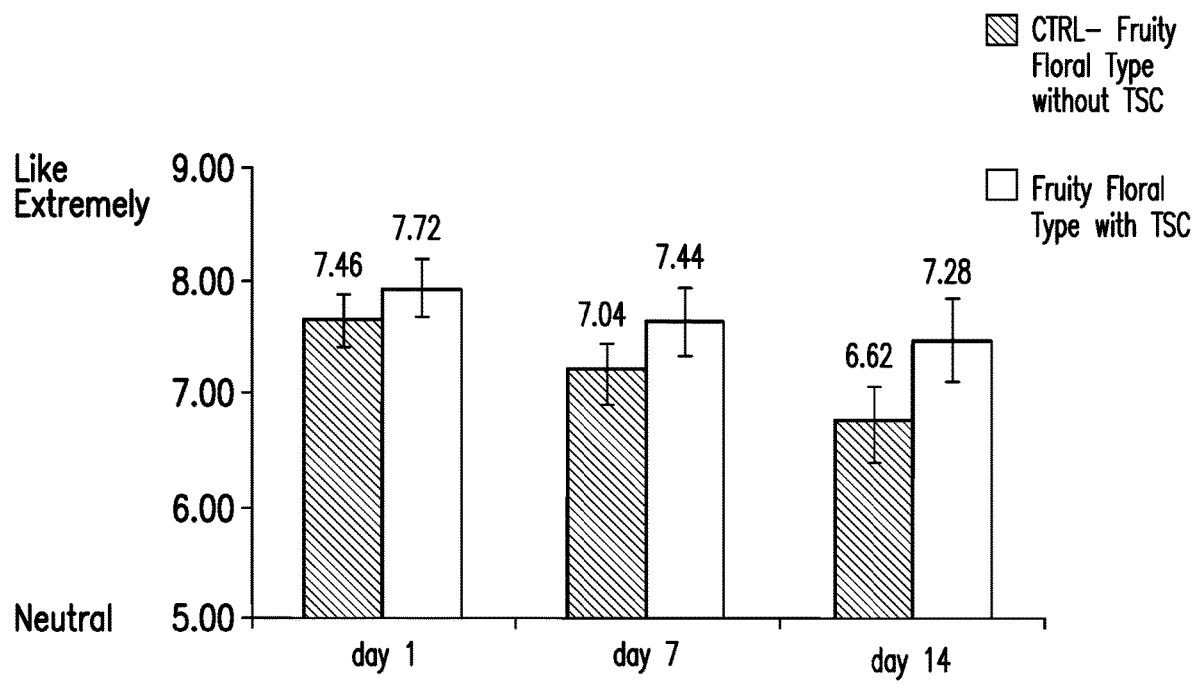
FIG. 8 depicts the results of the home use test of Example 12.
Figure 9A:
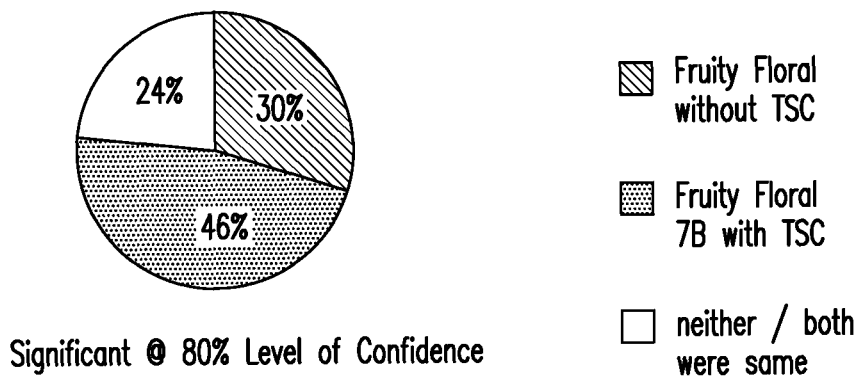
FIGS. 9a-9b depict comparison preferences of the products tested in Example 12. Specifically.
Figure 9B:
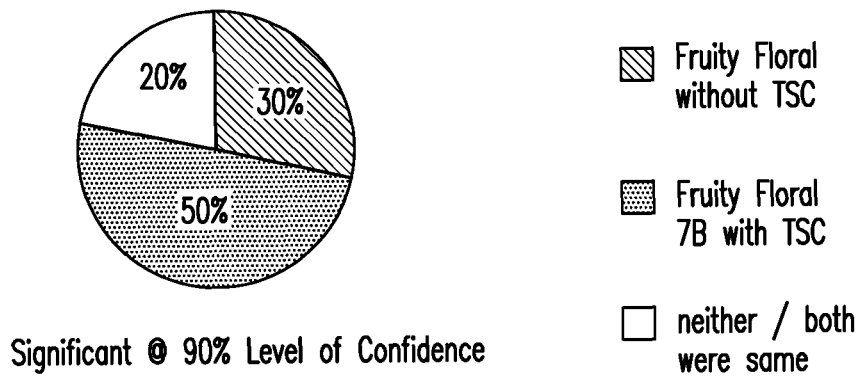

In this Example, air fresheners with a fruity/floral type fragrance, with and without TSC, were tested in the consumers' homes (N=50) by the same methods as Example 10. Results were collected on day 1, day 7, and day 14 of the home use test. FIG. 8 illustrates the overall opinion of the fragrance. The products containing TSC generated significantly higher liking scores at the 14 day time point than those that did not contain TSC. After using the products for 14 days, the consumers were asked additional preference questions comparing the control and fruity/floral type fragrance, with and without TSC. Consumer responses are summarized in FIG. 9a-b. These Figures illustrated that there is evidence that the addition of TSC reduces hedonic fatigue/habituation and was perceived as lighter and more airy.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the compounds and compositions of the disclosed subject matter without departing from the spirit or scope of the disclosed subject matter. Thus, it is intended that the disclosed subject matter include modifications and variations that are within the scope of the appended claims and their equivalents.

What is claimed is:

1. A fragrance composition comprising:
   a. at least two cooling compounds, wherein each cooling compound is selected independently from the group consisting of menthol, menthone, camphor, pulegol, isopulegol, menthyl lactate, p-menthane-3,8-diol, and mint oil;
   b. at least one of a warming compound or a tingling compound,
      wherein the warming compound is selected from the group consisting of vanillyl ethyl ether, vanillyl propyl ether, vanillyl butyl ether, vanillin, vanillyl alcohol, ethyl vanillin, ethyl vanillyl alcohol, gingerol, and ginger oleoresin; and
      wherein the tingling compound is selected from the group consisting of spilanthol, jambu oleoresin, black pepper extract, elemol, elemicin, lime oxide, and elemi oil; and
   c. an additional fragrance compound;
   wherein the at least two cooling compounds, the warming compound, and the tingling compound are trigeminal-stimulating compounds, and
   wherein the trigeminal-stimulating compounds are present in an amount effective to improve the hedonic experience, intensity, and noticeability of the fragrance composition to a user as compared to the fragrance composition in the absence of the trigeminal-stimulating compounds.

2. The fragrance composition of claim 1, wherein the fragrance composition comprises the two cooling compounds and the warming compound.

3. The fragrance composition of claim 1, wherein the composition comprises between about 1% and about 50% by weight of the at least two cooling compounds, the tingling compound, and the warming compound.

4. The fragrance composition of claim 3, wherein the composition comprises between about 5% and about 15% by weight of the at least two cooling compounds, the tingling compound, and the warming compound.

5. The fragrance composition of claim 1, wherein the composition further comprises one or more support materials.

6. The fragrance composition of claim 1, wherein the fragrance composition comprises the two cooling compounds and the tingling compound.

7. The fragrance composition of claim 6, wherein the fragrance composition further comprises the warming compound.

8. A fragrance combination comprising:
   a. a first fragrance composition comprising:
      (i) at least two cooling compounds, wherein each cooling compound is selected independently from the group consisting of menthol, menthone, camphor, pulegol, isopulegol, menthyl lactate, p-menthane-3,8-diol, and mint oil; and
      (ii) at least one of a warming compound or a tingling compound,
         wherein the warming compound is selected from the group consisting of vanillyl ethyl ether, vanillyl propyl ether, vanillyl butyl ether, vanillin, vanillyl alcohol, ethyl vanillin, ethyl vanillyl alcohol, gingerol, and ginger oleoresin; and
         wherein the tingling compound is selected from the group consisting of spilanthol, jambu oleoresin, black pepper extract, elemol, elemicin, lime oxide, and elemi oil;
      wherein the at least two cooling compounds, the warming compound, and the tingling compound are trigeminal-stimulating compounds; and
   b. a second fragrance composition comprising an additional fragrance compound,
   wherein the trigeminal-stimulating compounds are present in an amount effective to improve the hedonic experience, intensity, and noticeability of the fragrance combination to a user as compared to the fragrance combination in the absence of the trigeminal-stimulating compounds.

9. The fragrance combination of claim 8, wherein the first fragrance composition comprises the two cooling compounds and the warming compound.

10. The fragrance combination of claim 8, wherein the first fragrance composition comprises between about 1% and about 50% by weight of the at least two cooling compounds, the tingling compound, and the warming compound.

11. The fragrance combination of claim 10, wherein the first fragrance composition comprises between about 5% and about 15% by weight of the at least two cooling compounds, the tingling compound, and the warming compound.

12. The fragrance combination of claim 8, wherein the first fragrance composition comprises the two cooling compounds and the tingling compound.

13. The fragrance combination of claim 12, wherein the first fragrance composition further comprises the warming compound.

* * * * *